(12) United States Patent
Dong

(10) Patent No.: US 11,590,325 B2
(45) Date of Patent: Feb. 28, 2023

(54) URINARY CATHETER FOR WOMEN AND PERISTALTIC PUMP

(71) Applicant: BIOXIN MEDICAL CO., LTD., Weihai (CN)

(72) Inventor: Dongsheng Dong, Beijing (CN)

(73) Assignee: BIOXIN MEDICAL CO., LTD., Weihai (CN)

( * ) Notice: Subject to any disclaimer, the term of this patent is extended or adjusted under 35 U.S.C. 154(b) by 492 days.

(21) Appl. No.: 16/339,241

(22) PCT Filed: Jan. 19, 2018

(86) PCT No.: PCT/CN2018/073316
§ 371 (c)(1),
(2) Date: Apr. 3, 2019

(87) PCT Pub. No.: WO2019/007032
PCT Pub. Date: Jan. 10, 2019

(65) Prior Publication Data
US 2020/0030582 A1    Jan. 30, 2020

(30) Foreign Application Priority Data

Jul. 5, 2017    (CN) .......................... 201710540722.X

(51) Int. Cl.
*A61M 25/06* (2006.01)
*A61M 25/00* (2006.01)
(Continued)

(52) U.S. Cl.
CPC .......... *A61M 25/0662* (2013.01); *A61M 1/80* (2021.05); *A61M 25/0017* (2013.01);
(Continued)

(58) Field of Classification Search
CPC ................ A61M 25/0662; A61M 1/80; A61M 25/0017; A61M 25/10; A61M 2025/0681;
(Continued)

(56) References Cited

U.S. PATENT DOCUMENTS 5,368,575 A * 11/1994 Chang .................... A61M 25/02
604/351
5,376,094 A * 12/1994 Kline ................ A61M 25/0136
606/205
(Continued)

FOREIGN PATENT DOCUMENTS

CN    102029005 A    4/2011
CN    203736683 U    7/2014
(Continued)

OTHER PUBLICATIONS

The World Intellectual Property Organization (WIPO) International Search Report for PCT/CN2018/073316 dated Apr. 17, 2018 6 Pages.

*Primary Examiner* — Tatyana Zalukaeva
*Assistant Examiner* — Hans Kaliher
(74) *Attorney, Agent, or Firm* — Anova Law Group, PLLC

(57) ABSTRACT

The utility model discloses a urinary catheter for women and peristaltic pump, which comprises a body tube with an inner surface and an outer surface, and further comprises an external urethral orifice fixing part which can at least sleeve the catheter tip end inside when applied, a flexible urethral guide part, a urinary catheter driving part sleeved with the cylindrical body of the external urethral orifice fixing part, a hydrophobic part for leakage stop at the urinary outlet of the urinary catheter, a thin segment, a pump tube, a tube bed and other special structures for dilating the narrowed part of the urethra, which not only eliminate the defect of the traditional "non-guided suspended placement" in a safe
(Continued)

mode of "US-guided adjacent placement" and completely avoid contamination of the urinary catheter by the periurethral tissue, but also avoid the injury of urethral intima caused by urethral stricture in the placement procedure to the greatest extent; avoid contamination of the urinary catheter outlet by urine outflow; effectively clear the blockage of urine inlet due to blood clots and tissue masses in bladder during indwelling, and can also minimize the residual urine volume when used in conjunction with a special peristaltic pump.

14 Claims, 28 Drawing Sheets

(51) Int. Cl.
*A61M 1/00* (2006.01)
*A61M 25/10* (2013.01)
(52) U.S. Cl.
CPC ..... *A61M 25/10* (2013.01); *A61M 2025/0681* (2013.01); *A61M 2202/0496* (2013.01)
(58) Field of Classification Search
CPC ........ A61M 2202/0496; A61M 1/0058; A61M 2210/1092; A61M 25/0111; A61M 25/0067; A61M 2025/0063; A61M 25/01; A61M 5/31; A61F 5/455
See application file for complete search history.

(56) References Cited

U.S. PATENT DOCUMENTS

| | | |
|---|---|---|
| 2005/0015076 A1* | 1/2005 | Giebmeyer ........ A61M 25/0111 604/544 |
| 2005/0090779 A1* | 4/2005 | Osypka ............. A61M 25/0097 604/160 |
| 2006/0025753 A1* | 2/2006 | Kubalak ........... A61M 25/0017 604/544 |
| 2015/0039014 A1* | 2/2015 | Schaeffer ......... A61B 17/12104 606/199 |
| 2016/0310711 A1 | 10/2016 | Luxon et al. |
| 2017/0274176 A1* | 9/2017 | Kelly ..................... B65B 55/16 |
| 2018/0008804 A1* | 1/2018 | Laniado ........... A61M 25/0017 |
| 2018/0126126 A1* | 5/2018 | Ornelas Vargas .... A61M 39/10 |
| 2019/0232019 A1* | 8/2019 | Dong ................ A61M 25/0043 |

FOREIGN PATENT DOCUMENTS

| | | |
|---|---|---|
| CN | 206167605 U | 5/2017 |
| CN | 107185099 A | 9/2017 |

\* cited by examiner

URINARY CATHETER FOR WOMEN AND PERISTALTIC PUMP

FIELD OF THE UTILITY MODEL

The utility model relates to a urinary catheter, in particular to a urinary catheter for women and peristaltic pump, belonging to the technical field of medical devices.

BACKGROUND OF THE UTILITY MODEL

Urinary catheter is the most common medical device in clinic, which can drain urine from the bladder to the outside after it is inserted into the body via the urethra, and can be removed after one urine drainage, or can be retained for multiple drainage for prolonged period.

However, the urinary catheterization and its retention will lead to lower urinary tract injury to varying degrees, while lower urinary tract injury is more likely to cause or aggravate lower urinary tract infection and further affect lower urinary tract or even systemic organ function.

The female urethra is much shorter than the male urethra and is only 4 cm long, and the structure around the external urethral orifice is complicated, so even if the urinary catheter is not inserted, females are more susceptible to urinary tract infections. In the existing clinical procedure of female urethral catheterization, after the sterilization of the external urethral orifice and its surrounding tissues, usually use two fingers of one hand to press the periurethral tissue to make it relatively fixed, enlarge and expose the external urethral orifice, while use the other hand to hold the sterile urinary catheter directly or with tweezers, hemostatic forceps, etc., and slowly insert it from the external urethral orifice. When the urethra is bent or accompanied by stricture, it often needs to be inserted with force, which may lead to more serious injury to the urethra. When the urine inlet at the urinary catheter tip enters the bladder, the urine slowly flows out of the urine outlet of the urinary catheter outside the body into a container such as a kidney basin due to the pressure in the bladder, and then a successful catheterization can be expected. When indwelling is needed, immediately insert the urinary drainage bag connector into the urine outlet of the urinary catheter to form a closed system.

Existing female patients have the following problems in urethral catheterization:

1. It is difficult for an operator to use his/her two fingers to fix and expose the external urethral orifice, especially in the case of ectopic urethral orifice caused by urinary tract infections or scar pulling at the lateral incision, atrophy of the external urethral orifice and even entrapment in the anterior wall of the vagina in older women. Poor fixation and exposure of the external urethral orifice not only reduces the success rate of catheterization, but also greatly increases the urethral injury during the procedure.

2. Microorganisms near the female external urethral orifice, such as on the surface of labia majora and labia minora can easily contact and contaminate the urinary catheter outer surface that meanders into the urethra, thus bringing microorganisms into the urethra and bladder. Such extraluminal infection, i.e., the infection caused by a route outside the urinary catheter inner cavity, is the main cause of early urinary tract infection in patients with indwelling catheters.

3. The way of holding the urinary catheter with fingers or tweezers and hemostatic forceps to exert force unsupported results in the direction of force applied difficult to be the same as the urethral centerline due to the flexibility and meandering of the urinary catheter, and the operating force parallel to the urethral centerline is only a component of the force applied because of the direction of meandering at an angle to the direction of force applied, so a larger force is required to insert the urinary catheter, thus causing greater urethral injury and it would be more difficult to operate accurately when there is a bend in the external urethral orifice.

4. When the urinary catheter tip end travels to the stricture of the urethra, it usually needs to increase the force to push it forward and shear with the urethral intima in the stricture. Even if it passes through the stricture, the urethral intima will suffer severe contusion and create conditions for microbial infection.

5. Before the urinary catheter is judged to be inserted in the bladder, it is necessary to drain urine out of the urine outlet of the urinary catheter, then flow to containers such as a kidney basin and connect the drainage urine bag connector. Urine usually pollutes the connection between the urine outlet of the urinary catheter and the drainage urine bag connector. Microorganisms in the air or on the surface of surrounding objects may propagate in this part of the urine at the connection, and intraluminal contamination in the urinary catheter is easily caused when the drainage urine bag connector is removed and inserted again.

6. During the indwelling of the urinary catheter, insoluble blood clots and falling tissue lumps in the bladder due to changes in the state of illness will block the urine inlet of the catheter. The existing solution usually uses a guide wire to enter the urinary catheter inner cavity to dredge or a syringe to aspirate urine. If the effect is not desirable, a thicker catheter may be used instead and the patient may suffer from the pain of secondary catheterization.

7. Some patients have much urine left in the bladder due to bladder detrusor muscle weakness or decreased bladder compliance, which will make them more susceptible to infection. This situation requires nursing staff to use syringes to suck urine from the urinary outlet of the urinary catheter for many times, along with multiple removal and insertion of the drainage urine bag connector, which increases the risk of infection and makes the procedure cumbersome.

SUMMARY

In order to solve the above-mentioned seven deficiencies, the utility model provides a urinary catheter for women and peristaltic pump.

The object of the present utility model is achieved by:

A urinary catheter for women, comprising a hollow body tube made of solid material having an inner surface and an outer surface, in which the tube hollow is a urinary catheter inner cavity comprising a tip entering the bladder when applied, a tail left outside the body, and a middle section connecting the tip with the tail in which the tip is provided with a urine inlet and the tail is provided with a urine outlet; due to the wall thickness of the urinary catheter, the urine inlet has two openings, in which the inner surface opening is an inner cavity inlet immediately adjacent to the urinary catheter inner cavity; the outer surface opening is an outer cavity inlet, which is close to the bladder cavity when applied, and is characterized by further comprising an external urethral orifice fixing part which can at least sleeve the urinary catheter tip end inside when applied, wherein the external urethral orifice fixing part body is a hollow cylinder with a top end opening and a tail end opening, and the inside cylindrical hollow allows the urinary catheter tip and at least a part of the urinary catheter middle section to pass through; when it is used, the external urethral orifice fixing part at the top end opening side is pressed against the periurethral tissue of the body, so that the position of the external urethral orifice is fixed inside the external urethral orifice fixing part top end opening.

Because the female urethra is relatively short and straight, as shown in FIG. 3, with the traditional method of urinary catheterization and if good effects are achieved with the fixation of the external urethral orifice, the external urethral orifice center point may be located in the relatively vertical urethral centerline, and the urinary catheter tip end placed in this case may be easy to follow the vertical urethral centerline, causing minimal injury to the urethra intima and also minimal pain to patients; as shown in FIG. 4, if no good effects are achieved with the fixation of the external urethral orifice, the external urethral orifice center point may significantly deviate from the vertical urethral centerline, and the urinary catheter tip end placed in this case may be pressed vertically or nearly vertically toward the urethra intima, and cannot smoothly move along the vertical urethral centerline, causing major or serious injury to the urethra intima and thus causing greater pain to patients.

Even if good effects are achieved with the fixation of the external urethral orifice using the traditional method, as shown in FIG. 7, the catheter is clamped with tools or fingers and inserted into the external urethral orifice with the catheter suspended at a certain distance from the external urethral orifice. Resistance is encountered when the urinary catheter tip end contacts the external urethral orifice. Due to the flexibility of the catheter material, it is easy to bend, and the bending direction is extremely uncertain, either up or down or left or right, so that the catheter tip centerline cannot overlap with the urethral centerline but form an angle α. As shown in FIG. 8, the curved catheter tip end point cannot move along the vertical urethral centerline, but is pressed vertically or nearly vertically toward the urethral intima inside the external urethral orifice, causing major or serious injury to the urethral intima, and the injured urethral intima is susceptible to secondary bacterial infection.

The application of the fixing part of the urinary catheter for women according to the present utility model not only facilitates the fixation and exposure of the external urethral orifice, but also enables the external urethral orifice to be located in the fixing part top end opening while the urinary catheter tip is sleeved in the fixing part, so the starting point of the movement of the urinary catheter tip end is the position of the external urethral orifice, and the placement of the urinary catheter becomes a real "proximal placement", and the said proximal refers to the access to the external urethral orifice; further, since the cylindrical fixing part body has a certain length, it plays a role of movement guidance to the urinary catheter in it, so that the placement of the urinary catheter is further "US-guided proximal placement", thus avoiding the bending of the urinary catheter, making the urinary catheter tip centerline overlap with the urethral centerline, and the urinary catheter tip end is prone to moving along the vertical urethral centerline, which causes minimal damage to the urethral intima, and minimizes the pain of patients, thus completely eliminating the corresponding drawbacks of the traditional method of "non-guided suspended placement".

In order to facilitate the operation, the external urethral orifice fixing part may be provided with a finger holding portion protruding from the outer surface thereof, and the finger holding portion may be a boss, a handle, or a ring connected to the cylindrical body.

In order to achieve the purpose of fully fixing and fully exposing the external urethral orifice, at least two salient independent support legs having a smaller volume than that of human fingers are arranged on one side of the top end opening of the external urethral orifice fixing part. When it is used, the support leg free end is pressed against the periurethral tissue of the body, so that the position of the external urethral orifice is fixed and the external urethral orifice can be enlarged to facilitate entry of the urinary catheter tip end.

Compared with the conventional method of fixing and exposing the external urethral orifice with two fingers commonly used in existing clinical operations, the use of two or more independent support legs having a volume smaller than that of human fingers to press against the periurethral tissue, not only eliminates the dependence of such operation on human hands, and the effect of the support legs having a volume smaller than that of human fingers and having a hardness larger than that of human finger skins to fix the external urethral orifice is more accurate and reliable, and the effect of enlarging the external urethral orifice is more remarkable.

Further, a protruding and integrated annular support leg including oval rings is provided on one side of the top end opening of the external urethral orifice fixing part; the free end of the annular support leg may be planar, convex and/or concave; when it is used, the free end of the annular support leg is pressed against the body's periurethral tissue, so that the position of the external urethral orifice is fixed and the external urethral orifice can be enlarged to facilitate entry of the urinary catheter tip end.

Compared with two or more independent support legs, the annular support leg is circumferentially pressed against the periurethral tissue with a more reliable fixing effect and prevents the periurethral tissue from penetrating via the gap between the independent support legs, thereby eliminates the risk of contamination of the urinary catheter outer surface by the periurethral tissue that may be penetrated. It is also possible to adopt an annular support leg with an oval free end anatomically conforming to the shape of the body's periurethral tissue, so as to minimize the resistance when pressing against the surface of the human body tissue and better prevent surrounding tissues from contacting the urinary catheter outer surface. In order to better conform to the shape of the target periurethral tissue, the oval free end of the annular support leg may also be a non-planar concave or convex surface or a combination of concave and convex surfaces, which can be used for three-dimensional force application to better enlarge the external urethral orifice.

In order for the urinary catheter to better enter the urethra, a flexible urethral guide part capable of at least partially penetrating into the urethra and comprising two end openings of the hollow is provided on one side of the top end opening of the external urethral orifice fixing part, wherein, the urethral guide part has a tapered shape in which the bottom end tapers toward the top end, and the bottom end is sleeved outside the top end opening of the external urethral orifice fixing part; when it is used, the lateral surface of the urethral guide part comes in contact with the urethral intima and the medial surface comes in contact with the outer surface of the urinary catheter protruding from the top end opening of the external urethral orifice fixing part.

In some cases, such as undesirable patient posture or poor space position feeling of operators, even with the "US-guided adjacent placement" provided by the present utility model described above, although the catheter tip is easy to advance along the vertical urethral centerline, it does not have a catheter tip of sufficient length to enter the urethra at the very beginning, so it cannot play the guiding role of the urethra itself to the catheter inside it. The urethral intima is made of a material softer than that of the catheter and cannot effectively correct possible deviations during the procedure, so it is difficult to ensure that the catheter tip centerline completely overlaps with the urethral centerline. The most ideal way is to have a part, i.e. the urethral guide part, probing into a portion of the urethra in advance, with the catheter tip end advancing along this part to ensure that it is guided to the urethral centerline, while avoiding damage to the urethral intima caused by the catheter tip end due to the direction deviation, and the catheter tip end does not directly press against the urethral intima when the direction deviation occurs, but slides on the guide part medial surface.

When it is used, the urinary catheter tip enters the inner hollow of the urethral guide part from the top end opening of the external urethral orifice fixing part, slides forward along the guide part medial surface, extends out from the top end of the urethral guide part, enters the urethra and touches the urethral centerline, continues to move forward in the direction of the bladder along the vertical urethral centerline under the guidance of the urethra, thus achieving better docking with the urethra and exerting the guiding role of the urethra, and adjusting the tilting angle of the cylindrical body of the fixing part at any time according to the resistance suffered in the advancing process, which further improves the accuracy and success rate of the urinary catheterization, and also further reduces possible injury to the urethral intima.

The urethral guide part can be valviform to facilitate the outward dilatation and deformation of the urinary catheter as it passes through. It may also be a tapered part bent to one side as a whole, facilitating access to the biased external urethral orifice and/or curved urethra.

Further, the cylindrical body of the external urethral orifice fixing part is extended, and the length of the catheter that can be accommodated in the extended external urethral orifice fixing part is greater than or equal to the length L of the catheter that is located in the bladder and urethra when the catheter is retained. Such design of lengthening the cylindrical body of the external urethral orifice fixing part ensures that the portion of the urinary catheter entering the bladder and the urethra does not contact with the periurethral tissue during the insertion of the urinary catheter, and completely eliminates the risk of urinary tract infection caused by the periurethral tissue contaminating the urinary catheter outer surface. When the existing technique of lubricating the coating on the urinary catheter outer surface is applied, lubricating substances such as chitosan, sodium hyaluronate and the like can be coated on the urinary catheter outer surface of this length L.

Another consideration is that in order to adapt to the stricture, deflection of the external urethral orifice and even curvature of the urethra of some patients, the top end opening portion of the external urethral orifice fixing part is at a certain angle to the cylindrical body from the point of view of easy operation and reduction of injury, or the urethral guide part may be at a certain angle to the top end opening of the external urethral orifice fixing part. The top end opening portion of the external urethral orifice fixing part and the cylindrical body may also be a steerable connection including a bellows, and the said steerable connection refers to a connection with an adjustable connection angle.

Further, it also comprises a catheter driving part with a rod-shaped body sleeved with the cylindrical body of the external urethral orifice fixing part, wherein, one end of the rod-shaped body of the driving part is a tip sleeved with the cylindrical body of the external urethral orifice fixing part, which is slideable and conformal fit with the cylindrical body, while the driving part tail is far away from the fixing part, and at least one force application portion is arranged on the inner surface of the driving part tip and a force bearing portion is arranged on the catheter wall at the corresponding position.

The force application portion may be either partially convex or an annular boss or recess, while the force bearing portion may be either convex or an annular boss or a recess matched with the force application portion. When it is used, if the driving part moves toward the external urethral orifice, the urinary catheter is driven by the driving part to do synchronous movement and get into the urethra. When the driving part moves in the opposite direction to the external urethral orifice, the urinary catheter can be driven by it to withdraw from the urethra.

In practice, the body of the urinary catheter driving part can be hollow and rod-shaped or cylindrical, or semi-arc rod-shaped or bent rod-shaped in a fit with the bent fixing part.

Further, it also comprises a return spring, which is sleeved between the vicinity of the top end opening of the external urethral orifice fixing part and the catheter driving part, especially the driving part tip, to prevent the catheter driving part from moving toward the top end of the external urethral orifice fixing part.

The stationary end of the return spring is located near the fixing part top end opening, and its movable end abuts against the urinary catheter driving part tip.

If the urinary catheter encounters resistance when advancing in the urethra, it may be due to urethral stricture and/or curvature. Considering forced advancement will surely damage the urethra at this time, stop applying force, then the return spring can partially push off the driving part to drive part of the urinary catheter out of the urethra. Adjust the direction or take other measures such as adding lubricating oil before operation again.

One alternative to the return spring is to provide two rings near the tail end opening of the cylindrical body of the external urethral orifice fixing part and one ring at the driving part tail.

In order to separate the external urethral orifice fixing part and the driving part from the catheter after the catheter is inserted, the external urethral orifice fixing part and the driving part are openable and closable.

The said openable and closable means that, with respect to the urinary catheter confined in it, after the procedure of inserting the urinary catheter into the bladder is completed, the external urethral orifice fixing part and the driving part, which are respectively composed of at least two parts, are opened, so that the fixing part and the driving part are separated from the part of the urinary catheter left outside the body.

A urethral guide structure similar to the above-mentioned urethral guide part functions is to extend the outward taper of the urinary catheter tip end portion, and the taper extension portion extends from the top end opening of the external urethral orifice fixing part to probe into the external urethral orifice first and guide the catheter tip to move forward.

The taper extension portion of the urinary catheter tip end can be first inserted into the urethra when in use, to guide the urinary catheter tip to move forward along the urethral centerline, playing a similar role to the urethral guide part, and can be used independently or in conjunction with the urethral guide part.

In order to cope with possible urethral strictures during catheterization, the outer surface of the urinary catheter tip end is connected with a nipple-shaped flexible and hollow thin segment, and the hollow inside the thin segment is a thin segment inner cavity, one side of the thin segment connected with the outer surface of the urinary catheter tip end is a thin segment bottom and the other side is a thin segment top; the thin segment bottom is connected with the tip end outer surface and is a connecting part of the thin segment, and the rest part including the thin segment top is the thin segment dilatable part; the thin segment inner cavity is specifically formed by the inner surface of the thin segment dilatable part and the part of the catheter tip end whose outer surface is covered by the thin segment dilatable part; the thin segment top of the urinary catheter is closed to the outside by the blind end, and the average outer diameter of the part between the farthest point of the thin segment top and the farthest point of the urinary catheter tip end is smaller than the maximum outer diameter of the urinary catheter tip end; the thin segment inner cavity is connected to the outside through at least one route on the urinary catheter wall, i.e., the thin segment inner cavity route, which has at least one thin segment inner cavity route inner opening connecting with the thin segment inner cavity and at least one thin segment inner cavity route outer opening connecting with outside space at the urinary catheter middle section or the urinary catheter tail, and the thin segment inner cavity route outer opening is located in the elastic balloon cavity of a hollow elastic balloon.

The thin segment is structurally an extension of the urinary catheter tip end. The direction of the said extension can be either along the catheter tip centerline, or parallel to the catheter tip centerline, or at a certain angle to the centerline, i.e. biased extension, sometimes the thin segment of biased extension is more easily into the urethra at the bend. When the catheter travels in the urethra and encounters the stricture, the tip end with a larger outer diameter cannot pass through, while the thin segment with a smaller outer diameter can enter the stricture of the urethra. At this time, pressing the elastic balloon will fill a certain volume of air and/or liquid in the inner cavity of the elastic balloon into the inner cavity of the thin segment through the route of the inner cavity of the thin segment, so that the thin segment is dilated and maintained for a certain period of time, and the generated thrust is vertically applied on the urethral intima at the stricture to dilate the urethra, similar to balloon dilatation of coronary arteries, and then the elastic balloon is slackened and the elastic restoring force of the elastic balloon sucks out the air and/or liquid in the inner cavity of the thin segment to expand. After the dilatation of the thin segment is relieved, continue to push the catheter forward and the catheter tip end is easy to pass through the dilated urethral portion.

In order to avoid the drawback of the traditional way of judging the urinary catheter placed in the bladder only after urine is drained out of the urine outlet of the urinary catheter and then flows to containers such as a kidney basin, the present utility model further comprises a hydrophobic membrane for leakage stop arranged at the urinary catheter tail that closes the urinary catheter inner cavity to the outside to prevent fluid but not air flow.

The periphery of the hydrophobic membrane for leakage stop can be hermetically connected with an annular fixing housing to form a leakage stop part, and the fixing housing is in a fit and hermetically connected with an annular recess on the inner surface of the catheter inner cavity at the tail of the catheter.

In order to facilitate the observation of urine, at least the catheter wall in the area near the hydrophobic membrane for leakage stop is transparent or partially transparent within reach of the eye.

Further, in order to ensure that the urine outlet of the urinary catheter is not polluted for a period of time before it is butted with the drainage urine bag connector, a section of the tail of the urinary catheter at the urine outlet of the urinary catheter is closed by a sealing element that is easy to open, and the urine outlet of the urinary catheter is located in a protective cavity sealed by the sealing element that is easy to open. The easily openable sealing element itself is made of a material through which air can easily pass.

The internal bladder pressure of the patient during urination is usually within 10 kPa, and a hydrophobic membrane made of PVDF, PES, PAN and other polymers having a bore diameter of 0.1-0.5 microns and a water-blocking pressure of 10-20 kPa may be used in the embodiments.

In order to ensure smooth drainage during catheter indwelling, at least one foreign liquid outlet is provided on the tube wall between the inner cavity inlet and the outer cavity inlet (1302) and/or in a region near the urine inlet of the urinary catheter; the foreign liquid outlet is connected with the foreign liquid inlet on the foreign liquid collateral branch of the urinary catheter tail through the foreign liquid route on the urinary catheter wall.

In order to facilitate the active drainage of urine and the injection of foreign liquid, a part of the tube connecting the main drainage branch (141) and/or the foreign liquid collateral branch at the urinary catheter tail is a pump tube which can be deformed and closed under local extrusion and can be restored if extrusion removed, and the said tube pipe is sleeved in a curved or vertical tube bed which can be directly embedded in a tube bed receiving cavity on a pump body of a rotor peristaltic pump or a finger peristaltic pump matched therewith.

Further, a peristaltic pump comprises a pump body, a peristaltic component and a power component, wherein, the pump body is provided with a receiving cavity which can accommodate a tube bed sleeved with a pump tube previously described herein.

The beneficial effects of the present utility model are:

1. The external urethral orifice fixing part with a hollow cylindrical body can upgrade the existing two-point fixing method of two bulky and soft fingers to a fine or even more stable circumferential fixing of the external urethral orifice, and the fixing is more reliable. The external urethral orifice is located in the hollow inside the fixing part, so that the exposure is more sufficient and accurate disinfection is facilitated. The urethral guide part that can be probed into the external urethral orifice helps guide the catheter tip end into the urethra and reduce mucosal damage. The finger holding part, especially the finger ring, makes the procedure more convenient.

2. The extended external urethral orifice fixing part can prevent the external surface of the urinary catheter entering the urinary bladder from being contaminated by microorganisms on the surface of tissues near the external urethral orifice, such as clitoris and labia majora and labia minor.

3. The driving part sleeved with the extended external urethral orifice fixing part can ensure that the direction of force application is consistent with the movement direction of the urinary catheter, especially when the urethra is not bent, the direction of force application is easier to be the same as the urethral centerline.

4. When the catheter tip end travels to the stricture of the urethra, the thin segment can be advanced into the stricture area, and pressing the elastic balloon can dilate the thin segment and push away the urethral intima at the stricture perpendicular to the urethral intima, which is helpful for the catheter to smoothly pass through the stricture and avoids the shear damage to the urethral intima caused by pushing along the direction parallel to the urethral centerline to the greatest extent.

5. On the premise of timely judging the success of urethral catheterization, the leakage stop part and the nearby transparent tube wall which close the urine outlet of the urinary catheter can avoid urine outflow, save the container for receiving urine, ensure the dry and clean urine outlet of the urinary catheter, and avoid urine pollution during the insertion of the urine drainage bag connector.

6. The sterile liquid sprayed from the foreign liquid outlet arranged on the tube wall between the inner cavity inlet and the outer cavity inlet of the urinary catheter can accurately break, tear or dislodge the clots, tissue masses and other obstructions missed at the urine inlet of the urinary catheter to ensure smooth drainage. In conjunction with the suction of urine by negative pressure, obstructions can be sucked out of the bladder.

7. The pump tube arranged at the tail of the urinary catheter, which can be deformed and closed by local extrusion and can be recovered after extrusion is eliminated, and the curved or vertical tube bed sleeved on it are convenient to be directly embedded in the tube bed receiving cavity on the pump body of the rotor peristaltic pump or finger peristaltic pump matched therewith, and can evacuate urine in the bladder via the negative pressure attraction generated by peristaltic pump operation to the maximum extent without reliance on the internal bladder pressure, and reduce the risk of infection and bladder injury caused by more residual urine. It is safer and more convenient than the procedure of using a syringe to aspirate several times and multiple removal and insertion of the drainage urine bag connector.

REFERENCE NUMBERS IN THE FIGURES

Figure 1:
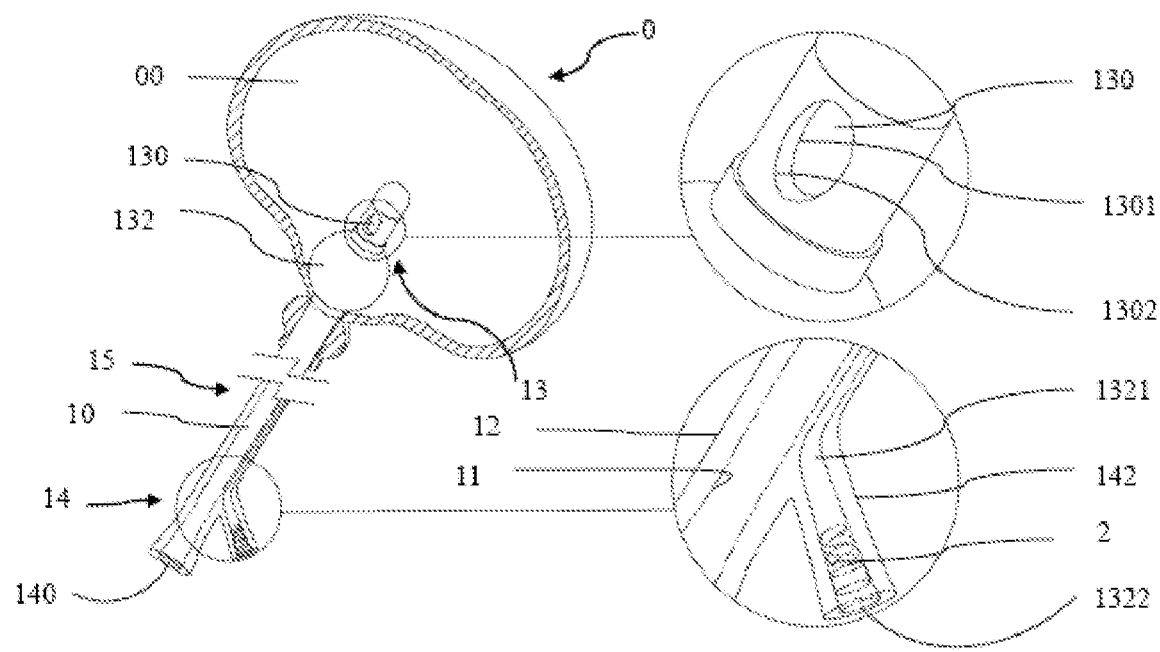
FIG. 1 is a structural schematic view of existing urinary catheters.

0. Bladder; 00. Bladder cavity; 01. Urethra; 010, 010a, 010b. Urethral inner cavity; 0100. External urethral orifice; 0101. Urethral centerline; 0102. External urethral orifice center point; 011. Urethral intima; 013. Periurethral tissue; 0131. Labium; 1. Urinary catheter; 10. Urinary catheter inner cavity; 11. Urinary catheter inner surface; 110. Annular recess of the urinary catheter inner surface; 111. Contaminant; 12. Urinary catheter outer surface; 121. Urinary catheter wall force bearing part; 13. Urinary catheter tip; 130. Urine inlet; 1301. Inner cavity inlet; 1302. Outer cavity inlet; 131. Urinary catheter tip end; 131p. Urinary catheter tip end farthest point; 1311. Thin segment inner cavity route inner opening; 1312. thin segment inner cavity route; 1313. Thin segment cavity route outer opening; 1315. Urinary catheter tip end point; 1316. Urinary catheter tip centerline; 1317. Urinary catheter tip end conical extension part; 1318. Tube wall between outer cavity inlet and inner cavity inlet; 132. Bladder fixing balloon; 1321. Bladder fixing balloon route; 1322. External opening of the filling collateral branch of the bladder fixing balloon; 14. Urinary catheter tail; 140. Urine outlet; 141. Main drainage branch; 1411. Urinary catheter tail end face; 142. Filling collateral branch of the bladder fixing balloon; 143. Filling collateral branch of the thin segment; 144. Foreign liquid collateral branch; 15. Urinary catheter middle section; 16. Thin segment; 160. Thin segment inner cavity; 161. Thin segment bottom; 1612. Thin segment dilatable part; 162. Thin segment top; 162p. Thin segment top farthest point; 17. Elastic balloon; 170. Elastic balloon inner cavity; 171. Elastic balloon external opening; 2. Non-return valve; 20. Foreign liquid outlet; 21. Foreign liquid route; 22. Foreign liquid inlet; 222. Hinge; 33, 33a, 33b. Blood clots; 4. Kidney basin; 4b. Urine retained on the catheter tail end face; 4c. Blocked urine; 5. Drainage urine bag connector; 6. Leakage stop part; 61. Fixing housing; 62. Hydrophobic membrane for leakage stop; 63. Opening seal; 65. Sealing element; 650. Protective cavity; 66. Pump body; 660. Rotor; 661. Roller; 662. Tube bed receiving cavity; 663. Rotary handle; 666. Return spring; 6661. Return spring stationary end; 6662. Return spring movable end; 67. Pump body cover; 68. Pump tube; 69. Tube bed; 7. Fixing part; 7a, 7b. Independent fixing parts; 7a1. Fixing part side end face groove; 7b1. Fixing part side end face rib; 7a2, 7b2. Connecting parts; 7b20. Connecting part bulge; 70. Fixing part cylindrical hollow; 71. Fixing part body; 71a, 71b. Fixing part two-piece body; 711. Fixing part top end opening; 712. Fixing part tail end opening; 7121. Fixing part guide slot; 713. Fixing part inner surface; 714. Fixing part body through slot; 7141. Through slot bottom end; 7142. Through slot top end; 715. Fixing part top end guide portion; 7151. Annular boss; 72. Holding portion; 721. Holding portion boss; 722. Holding portion handle; 723. Fixing part finger ring; 73. Independent support leg; 73a. Primary support leg; 73b. Secondary support leg; 731. Support leg free end; 732. Primary support leg rotating shaft; 733. Secondary support leg rotating shaft; 74. Annular support leg; 741. Annular support leg free end; 742. Oval support leg; 7421. Oval support leg free end; 75. Urinary catheter driving part; 75a, 75b. Independent urinary catheter driving part; 750. Guide part interior; 751. Guide part top end; 752. Guide part bottom end; 753. Guide part medial surface; 754. Guide part lateral surface; 755. Guide valve; 756. Curved urethral guide part; 8. Driving part; 80. Driving part tip medial surface; 81. Driving part rod-shaped body; 811. Driving part tip; 8111. Portion of the driving part tip inserted in the through slot; 8112. Anti-prolapse portion; 8113. Anti-prolapse portion top end face; 8114. Driving part tip end face; 8115. Driving part force application portion; 8116. Driving part tip top end face; 812. Driving part tail; 823. Driving part tail finger ring; L. The sum of the lengths of the urinary catheter located in the bladder and urethra when the urinary catheter is retained.

DETAILED DESCRIPTION OF EMBODIMENTS

Embodiment 1: the existing urinary catheter commonly used in clinical practice as shown in FIG. 1 is a hollow body tube made of solid material having a urinary catheter inner surface 11 and a urinary catheter outer surface 12, which is usually sterilized before use. The tube hollow is a urinary catheter inner cavity 10, comprising a urinary catheter tip 13 entering the bladder 0 during use, a urinary catheter tail 14 left outside the body and a urinary catheter middle section 15 connecting the urinary catheter tip 13 and the urinary catheter tail 14. The urinary catheter tip 13 is provided with a urine inlet 130, and the urinary catheter tail 14 is provided with a urine outlet 140. Because the catheter has a wall thickness, the urine inlet 130 has two openings, in which, the inner surface opening is an inner cavity inlet 1301, which is adjacent to the catheter inner cavity 10. The outer surface opening is an outer cavity inlet 1302, which is generally adjacent to the bladder cavity 00 during use. The bladder fixing balloon 132 for indwelling catheterization is located below the urine inlet 130 of the urinary catheter tip 13. A certain amount of air and/or liquid is injected into a non-return valve 2 at the external opening of the filling collateral branch of the bladder fixing balloon 1322 of the filling collateral branch of the bladder fixing balloon 142, through the bladder fixing balloon route 1321 in the catheter wall, making it difficult for it to prolapse from the bladder cavity 00.

Figure 2:
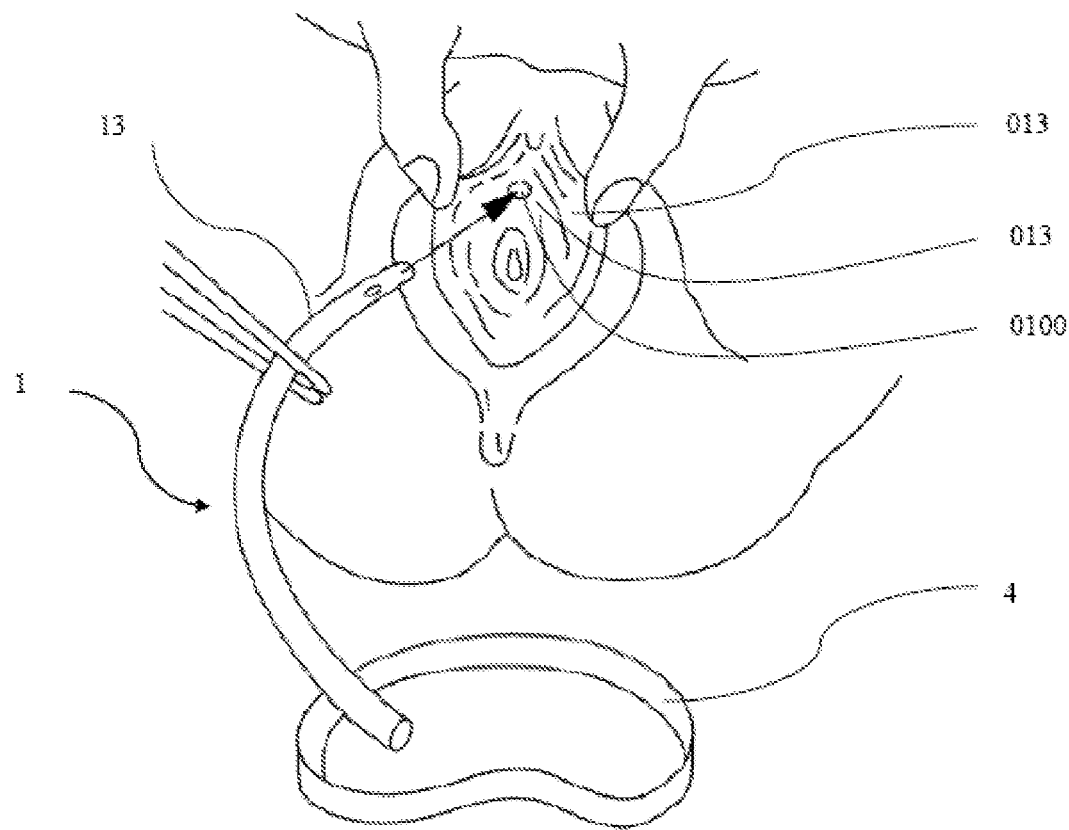
FIG. 2 is a schematic view of a fixing mode of an external urethral orifice in existing urethral catheterization procedure.
Figure 3:
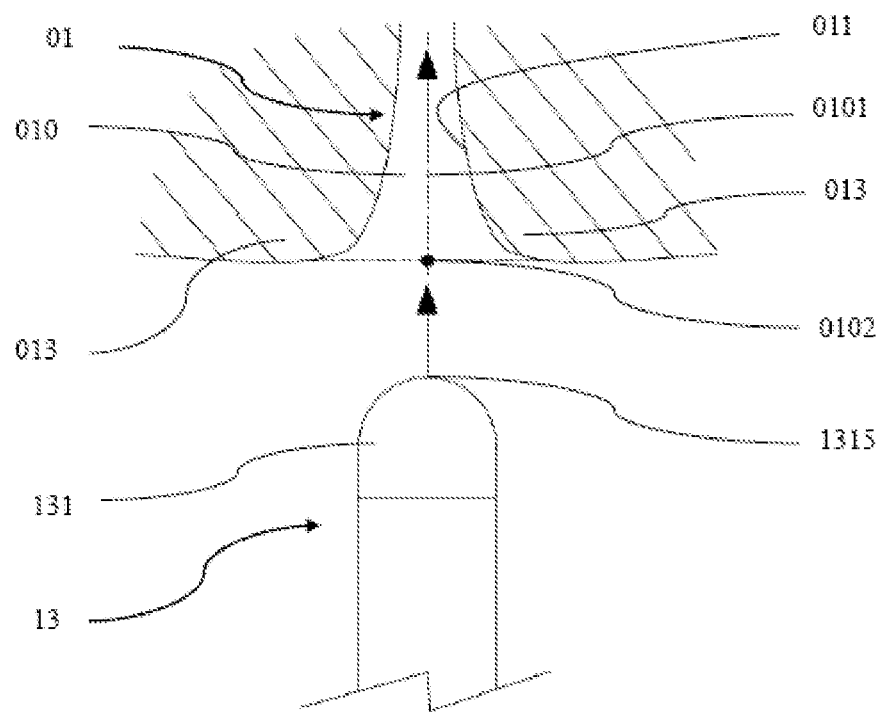
FIG. 3 is a schematic illustration of an external urethral orifice with desirable fixation effects.
Figure 4:
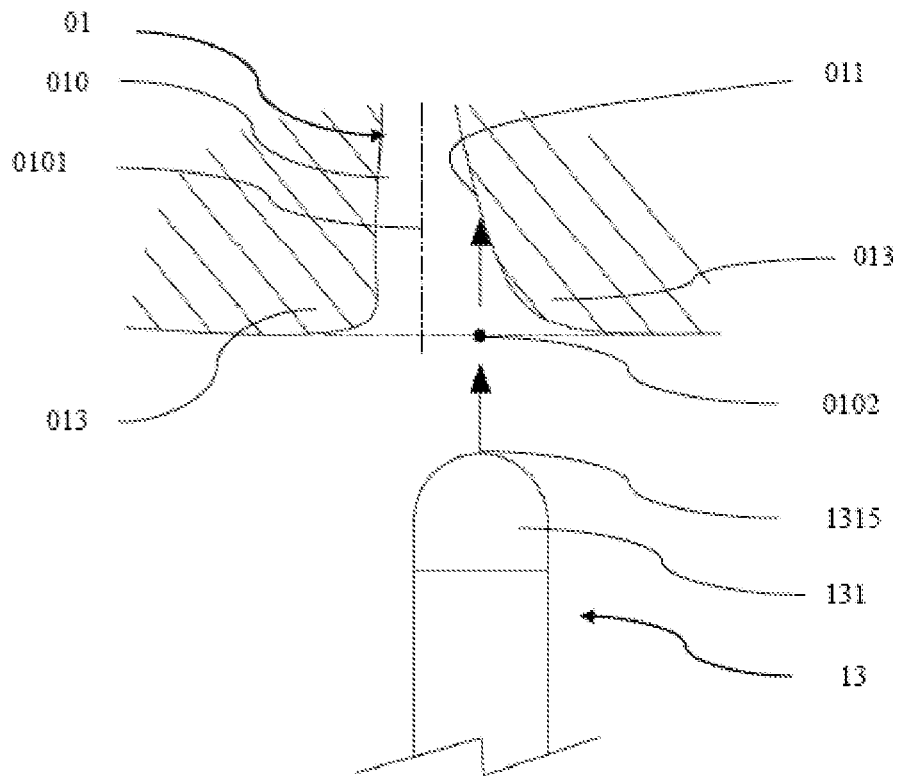
FIG. 4 is a schematic illustration of an external urethral orifice with undesirable fixation effects.

As shown in FIG. 2, usually we use two fingers to fix and expose the external urethral orifice 0100 clinically for female patients during the catheterization, hold the urinary catheter tip 13 with tools or fingers, and insert the urinary catheter suspended toward the external urethral orifice 0100 at a certain distance from the external urethral orifice 0100, with arrows in the figure indicating the direction of travel of the urinary catheter tip 13. Because the female urethra is relatively short and straight, as shown in FIG. 3, if good effects are achieved with the fixation of the external urethral orifice, the external urethral orifice center point 0102 may move forward along the relatively vertical urethral centerline 0101, and the urinary catheter tip end 131 placed in this case may be easy to follow the vertical urethral centerline 0101 to move forward, causing minimal injury to the urethral intima 011 and also minimal pain to patients. If no good effects are achieved with the fixation of the external urethral orifice, as shown in FIG. 4, the external urethral orifice center point 0102 may significantly deviate from the vertical urethral centerline 0101, and the urinary catheter tip end 131 placed in this case may be pressed vertically or nearly vertically toward the urethra intima 011, and cannot smoothly move along the vertical urethral centerline 0101, causing major or serious injury to the urethra intima 011 and thus causing greater pain to patients, with arrows in FIGS. 3 and 4 indicating the direction of travel of the urinary catheter tip 13.

Figure 7:
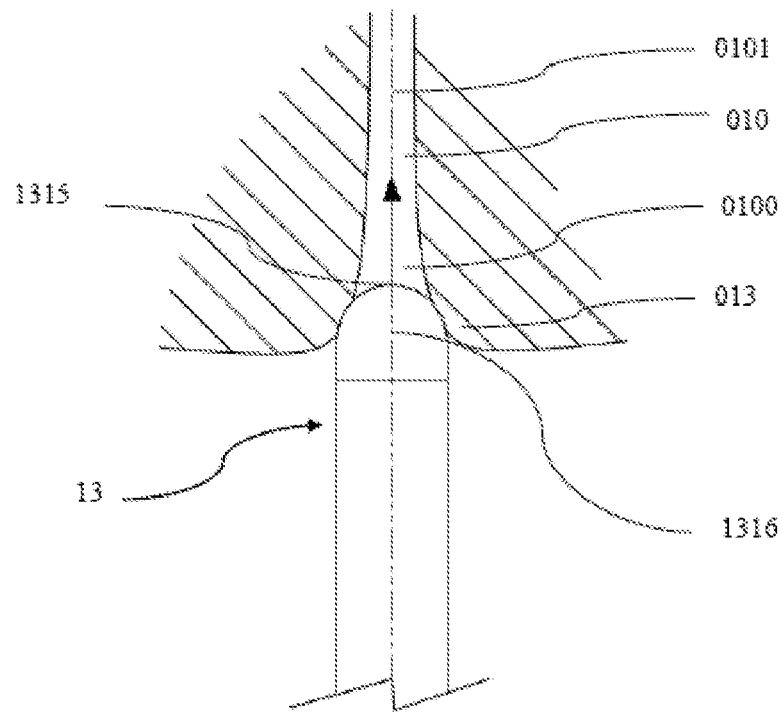
FIG. 7 is a schematic view of stress analysis of a catheter tip as it travels toward the external urethral orifice.
Figure 8:
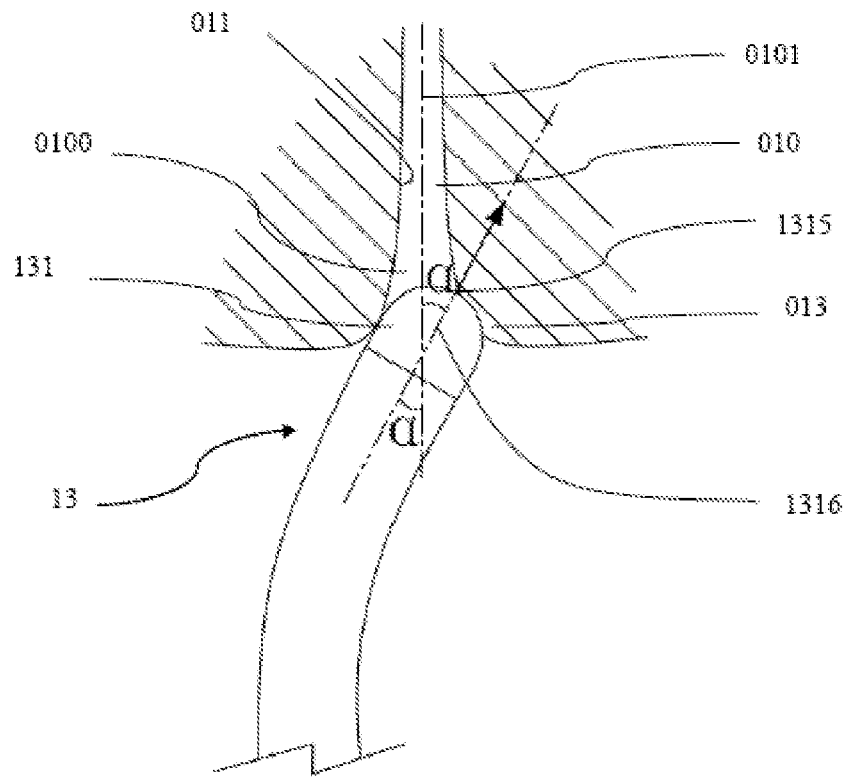
FIG. 8 is a schematic view of stress analysis of a catheter tip when it is subjected to resistance from the external urethral orifice.

According to the traditional method, even if good effects are achieved with the fixation of the external urethral orifice, as shown in FIG. 7, the catheter is clamped with tools or fingers and inserted into the external urethral orifice 0100 with the catheter suspended at a certain distance from the external urethral orifice 0101, with arrows in the figure indicating the direction of travel of the urinary catheter tip 13. As shown in FIG. 8, resistance is encountered when the urinary catheter tip end 131 contacts the external urethral orifice 0100. Due to the flexibility of the catheter material, it is easy to bend, and the bending direction is extremely uncertain or up or down or left or right, so that the catheter tip centerline 1316 cannot overlap with the urethral centerline 0101 but form an angle α. The curved catheter tip end point 1315 cannot move along the vertical urethral centerline 0101, but is pressed vertically or nearly vertically toward the urethral intima 011 inside the external urethral orifice 0100, causing major or serious injury to the urethral intima 011, and the injured urethral intima 011 is susceptible to secondary bacterial infection, with arrows indicating the direction of travel of the urinary catheter tip 13.

Figure 9:
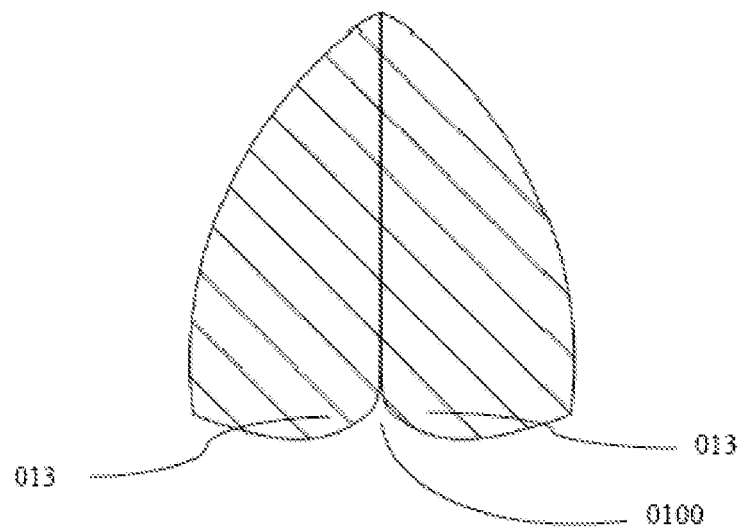
FIG. 9 is a schematic view of an external urethral orifice when it is closed.
Figure 10:
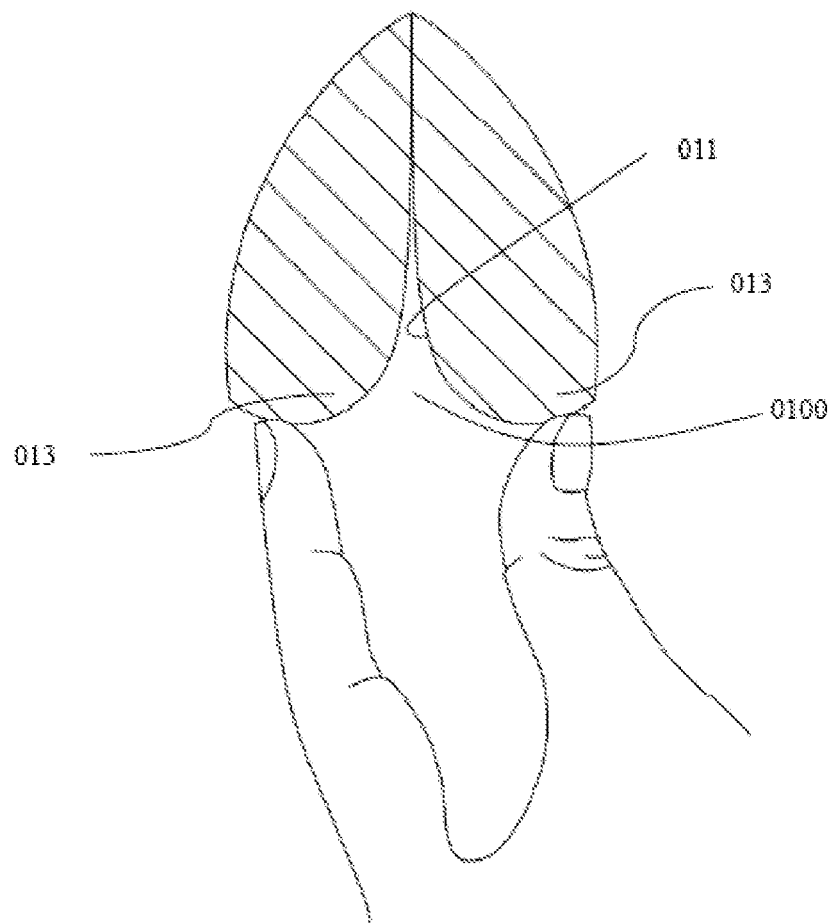
FIG. 10 is a schematic view of an external urethral orifice when it is opened.

FIG. 9 shows the unexposed external urethral orifice 0100, while FIG. 10 shows the external urethral orifice 0100 being dilated and exposed by the operator's two fingers, with its position relatively fixed.

Figure 11:
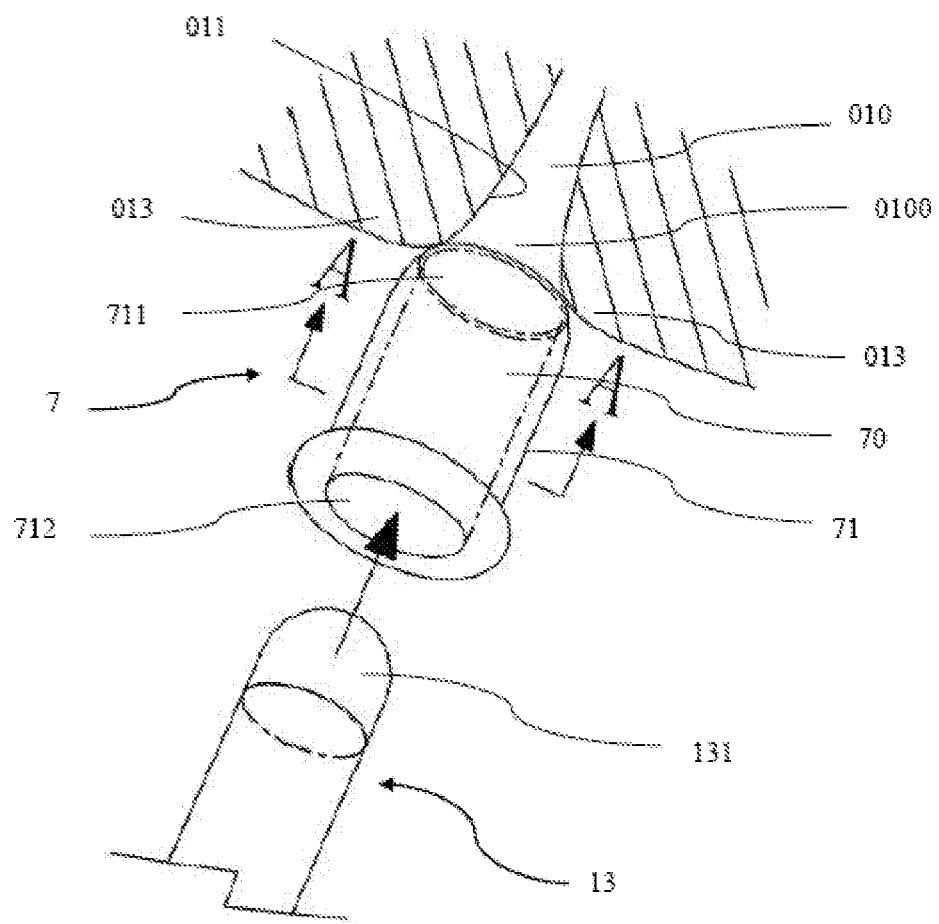
FIG. 11 is a schematic view of a fixing part according to Embodiment 1 of the present utility model.
Figure 12:
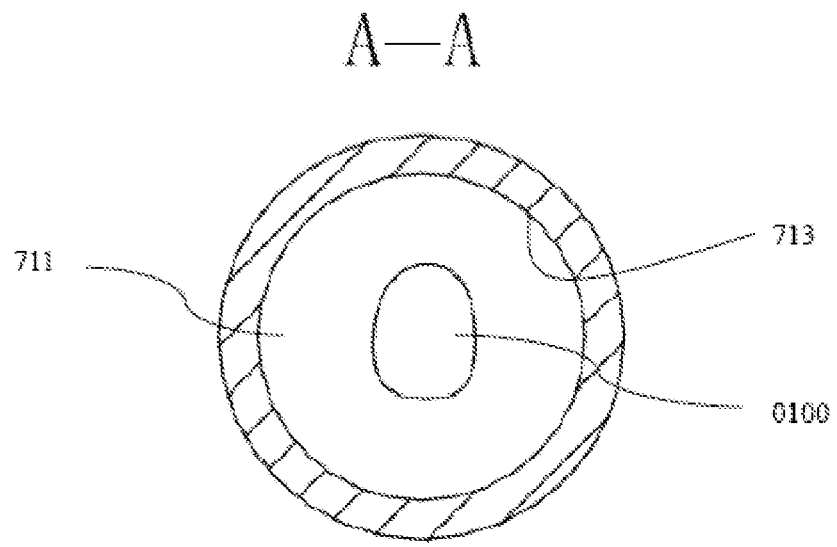
FIG. 12 is a plan view of FIG. 11 after section A-A is cut open in three dimensions according to Embodiment 1 of the present utility model.

As shown in FIG. 11, embodiment 1 of the urinary catheter according to the present utility model is provided with a fixing part 7 which can at least sleeve the urinary catheter tip end 131 inside when applied, wherein the fixing part body 71 of the fixing part 7 is a hollow cylinder with a fixing part top end opening 711 and a fixing part tail end opening 712, and the fixing part cylindrical hollow 70 allows the urinary catheter tip 13 and at least a part of the urinary catheter middle section 15 to pass through, with arrows indicating the direction of travel of the urinary catheter tip 13. When it is used, the fixing part (7) at the fixing part top end opening 711 side is pressed against the periurethral tissue 013 of the body's external urethral orifice 0100, so that the position of the external urethral orifice 0100 is fixed inside the fixing part top end opening 711 of the fixing part 7, as shown in FIG. 12.

Figure 13:
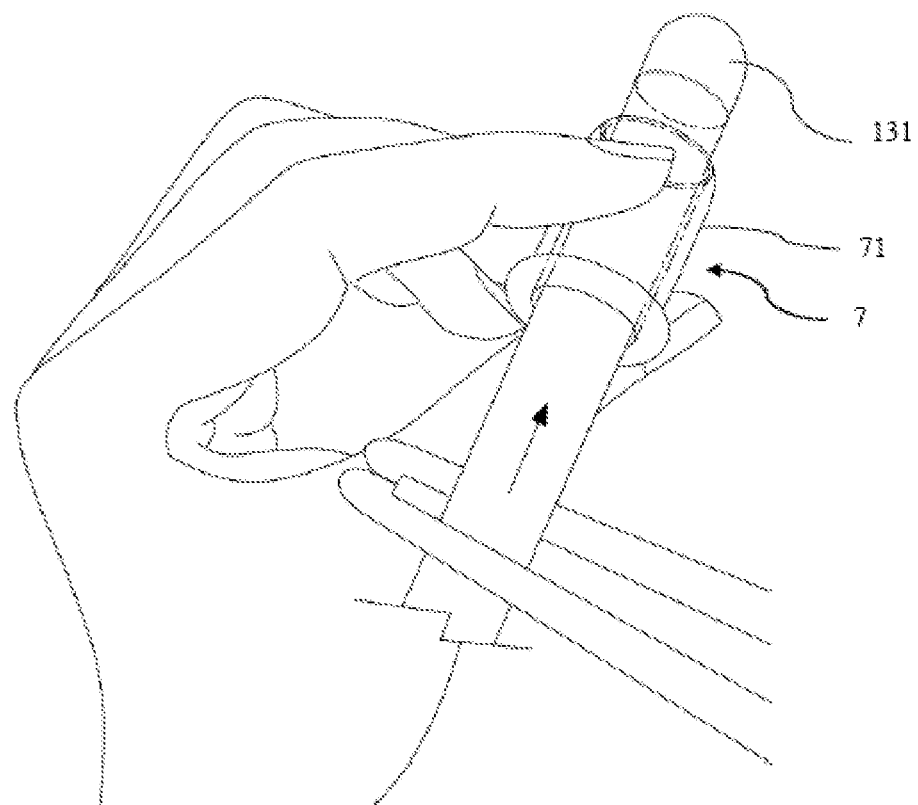
FIG. 13 is a schematic view of a fixing part when it is used according to Embodiment 1 of the present utility model.

The fixing part 7 not only facilitates the fixation and exposure of the external urethral orifice 0100 and when it is used, the external urethral orifice 0100 of patients is located in the fixing part top end opening 711 of the fixing part 7 while the urinary catheter tip 13 is sleeved in the fixing part 7, so the starting point of the movement of the urinary catheter tip end 131 is the external urethral orifice 0100, and the placement of the urinary catheter becomes a real "proximal placement", and the said proximal refers to the access to the external urethral orifice 0100; further, as shown in FIG. 13, since the cylindrical fixing part body 71 of the fixing part 7 has a certain length, it plays a role of movement guidance to the urinary catheter in it, so that the placement of the urinary catheter is further "US-guided proximal placement", thus avoiding the bending of the urinary catheter, making the urinary catheter tip centerline 1316 overlap with the urethral centerline 0101, and the urinary catheter tip end 131 is prone to moving along the vertical urethral centerline 0101, which causes minimal damage to the urethral intima 011, and minimizes the pain of patients, thus completely eliminating the corresponding drawbacks of the traditional method of "non-guided suspended placement", with arrows in the figure indicating the direction of travel of the urinary catheter tip 13.

Figure 14:
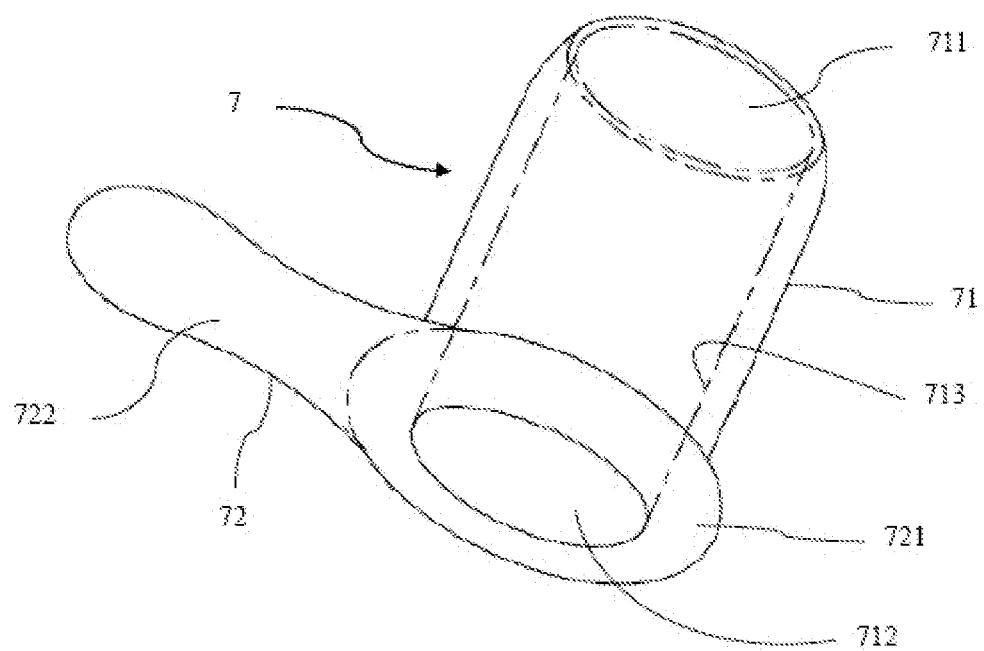
FIG. 14 is a schematic view of a fixing part according to Embodiment 2 of the present utility model.

Embodiment 2: as shown in FIG. 14, in order to facilitate operation, the fixing part 7 may be provided with a holding portion 72 protruding from the outer surface thereof, wherein, the holding portion 72 comprises a holding portion boss 721 and a holding portion handle 722 that may be connected to the fixing part body 71, although the fixing part body 71 may be directly held during use.

Figure 15:
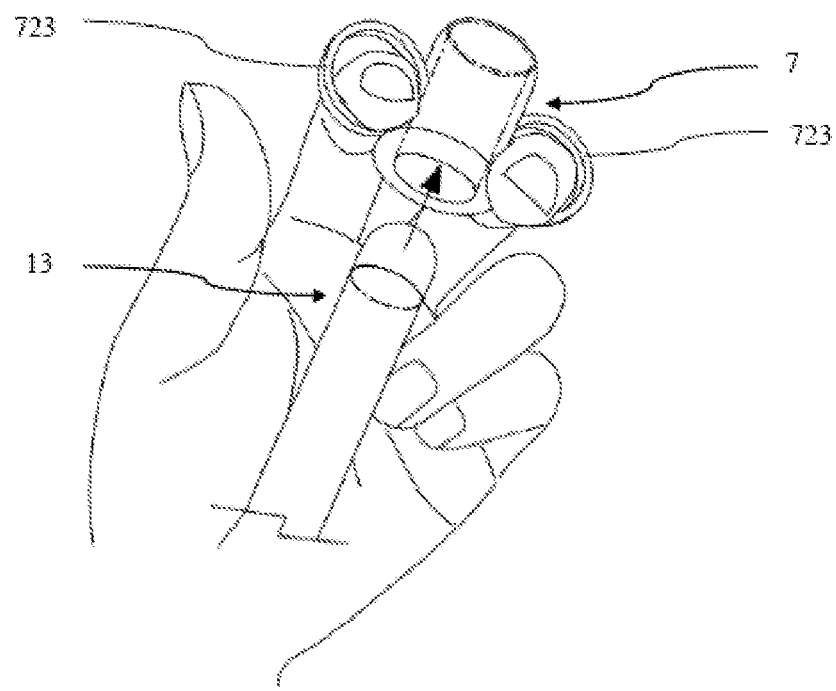
FIG. 15 is a schematic view of a fixing part according to Embodiment 3 of the present utility model.
Figure 16:
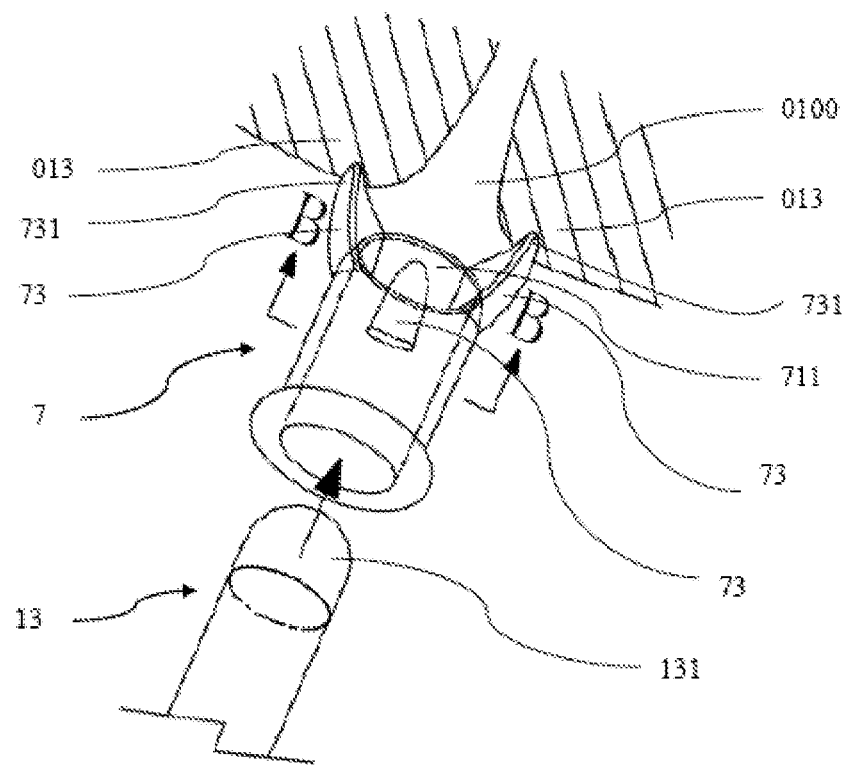
FIG. 16 is a schematic view of a fixing part support leg according to Embodiment 4 of the present utility model.

Embodiment 3: as shown in FIG. 15, the holding portion 72 protruding from the outer surface of the fixing part 7 of the present utility model is provided in the form of two fixing part finger rings 723, and the operation of placing fingers in the hollow of the fixing part finger rings 723 is more stable and reliable, and the arrows in the figure indicates the direction of travel of the urinary catheter tip 13.

Figure 6:
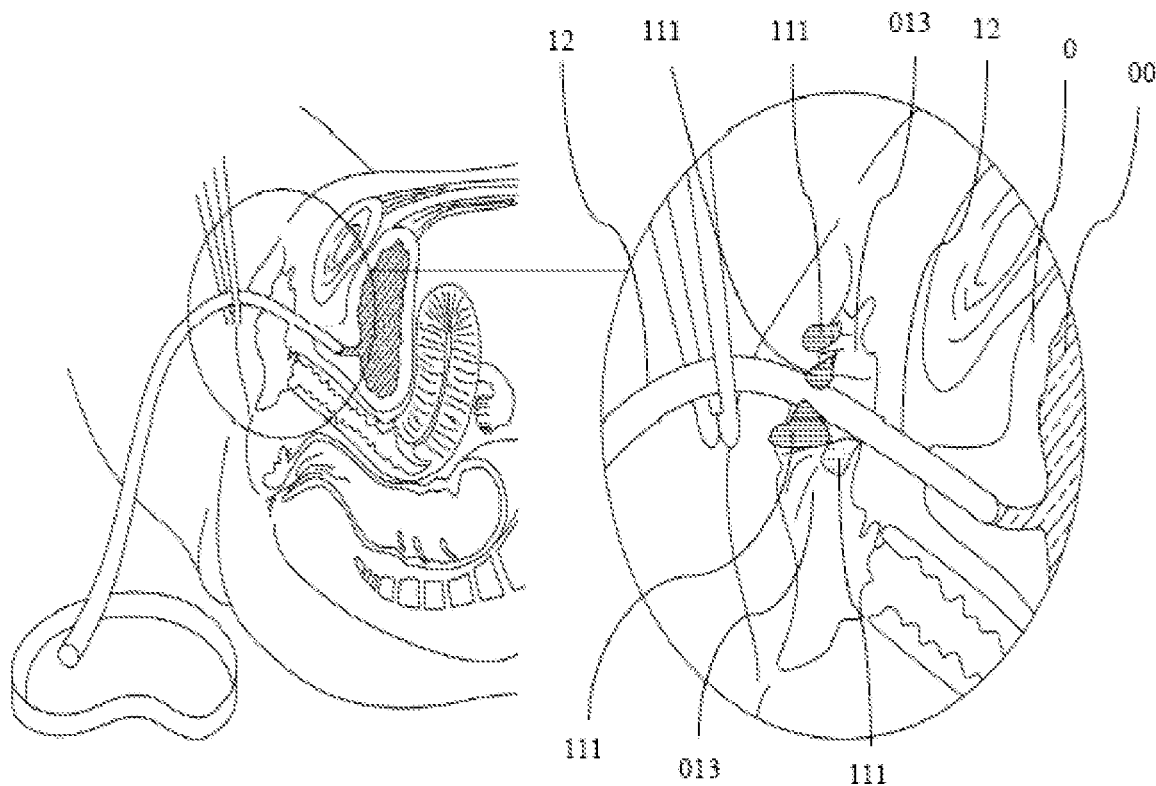
FIG. 6 is a schematic view of a urinary catheter outer surface contaminated by labial mucosa.
Figure 17:
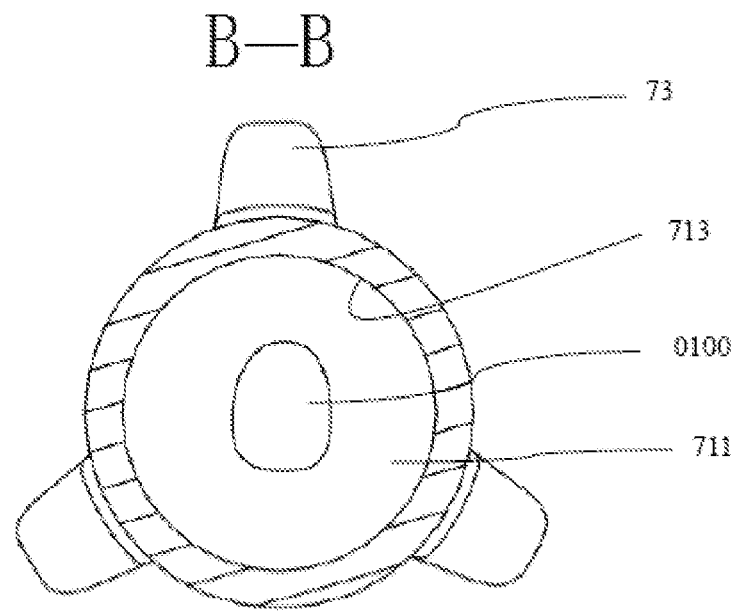
FIG. 17 is a plan view of a fixing part support leg of FIG. 16 after section B-B is cut open in three dimensions according to Embodiment 4 of the present utility model.

Embodiment 4: as shown in FIG. 6, in order to achieve the purpose of fully fixing and fully exposing the external urethral orifice 0100, three salient independent support legs 73 having a smaller volume than that of human fingers and having a hardness larger than that of human fingers are arranged on one side of the fixing part top end opening 711 of the fixing part 7. When it is used, the support leg free end 731 of the independent support leg 73 is pressed against the periurethral tissue 013 of the body's external urethral orifice 0100, so that the position of the external urethral orifice 0100 is fixed and the external urethral orifice can be enlarged to facilitate entry of the urinary catheter tip end 131, with arrows in the figure indicating the direction of travel of the urinary catheter tip 13. The external urethral orifice 0100 shown in FIG. 17 is located in the fixing part top end opening 711 to which the independent support leg 73 is attached.

Compared with the conventional method of fixing and exposing the external urethral orifice 0100 with two fingers commonly used in existing clinical operations, the use of two or more independent support legs 73 having a volume smaller than that of human fingers to press against the periurethral tissue 013 of the external urethral orifice 0100, not only eliminates the dependence of such operation on human hands, and the effect of the independent support legs 73 having a volume smaller than that of human fingers and having a hardness larger than that of human finger skins to fix the external urethral orifice 0100 is more accurate and reliable, and the effect of enlarging the external urethral orifice 0100 is more remarkable.

Figure 18:
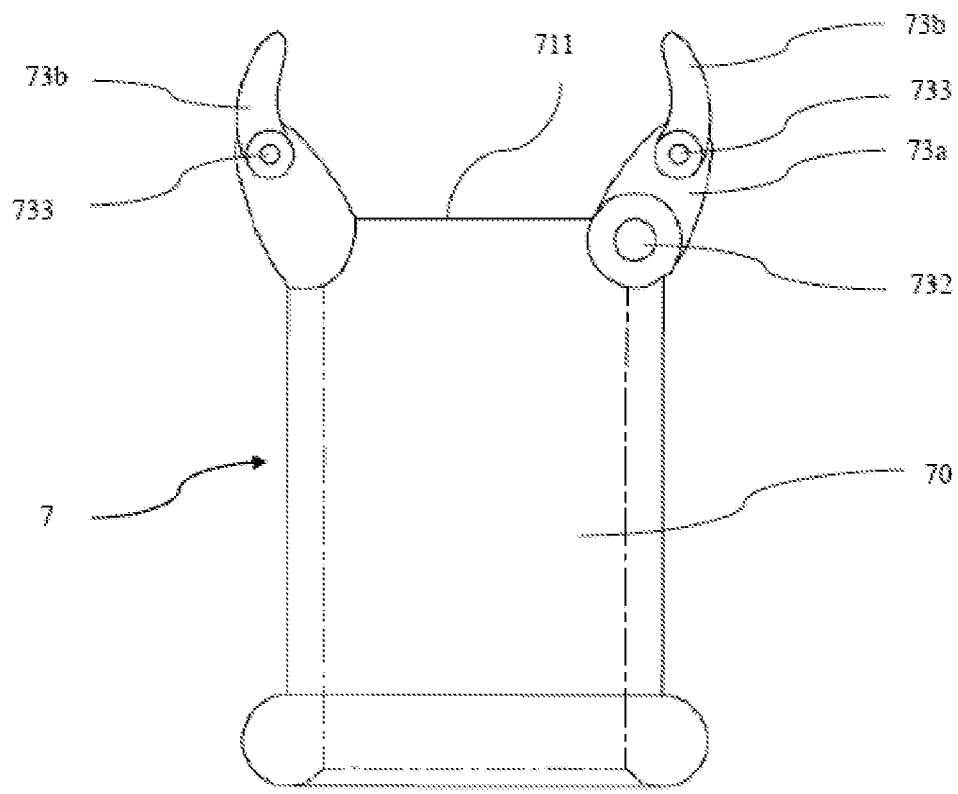
FIG. 18 is a schematic view of a fixing part adjustable support leg according to Embodiment 5 of the present utility model.

Embodiment 5: as shown in FIG. 18, a primary support leg 73*a* is provided at the edge of the fixing part top end opening 711 of the fixing part 7, and the right-handed primary support leg 73*a* is the primary support leg 73*a* connected to the cylindrical body top edge through a primary support leg rotating shaft 732. The primary support leg 73*a* is connected with a secondary support leg 73*b* with an adjustable angle. The secondary support leg 73*b* is connected with the primary support leg 73*a* through a secondary support leg rotating shaft 733. The primary support leg 73*a* and the secondary support leg 73*b* with an adjustable rotating angle can better adapt to the structure of the external urethral orifice 0100 and the periurethral tissue 013 of different patients.

Figure 19:
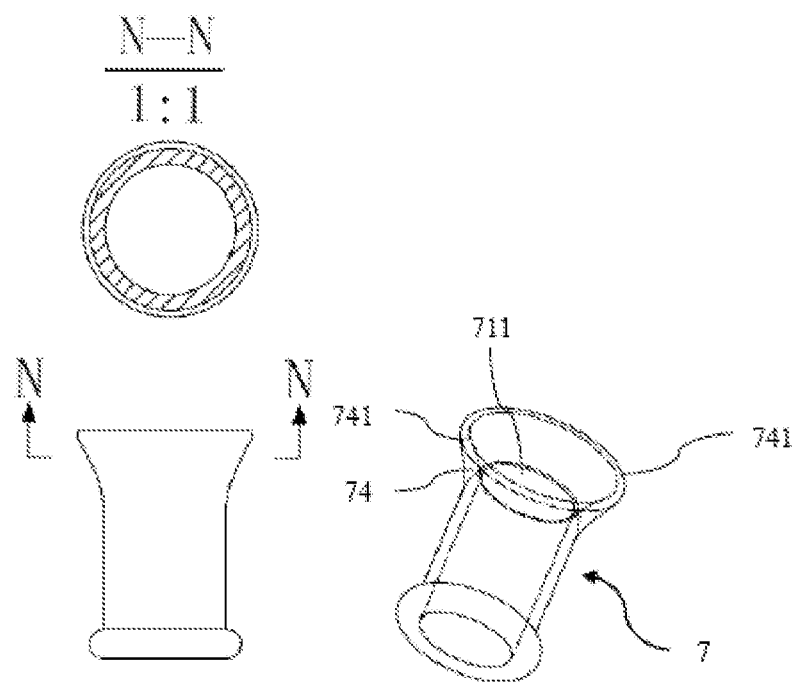
FIG. 19 is a schematic view of a annular support leg according to Embodiment 6 of the present utility model.

Embodiment 6: as shown in FIG. 19, a protruding and integrated annular support leg 74 is provided on one side of the fixing part top end opening 711 of the fixing part 7; when it is used, the annular support leg free end 741 of the annular support leg 74 may be pressed against the periurethral tissue 013 of the body's external urethral orifice 0100, convenient for the entry of the urinary catheter tip end 131; the annular support leg free end 741 of the annular support leg 74 can be planar, convex and/or concave, in order to adapt to the structure of the external urethral orifice 0100 and the periurethral tissue 013 of different patients.

Compared with two or more independent support legs 73, the annular support leg 74 is circumferentially pressed against the periurethral tissue 013 of the external urethral orifice 0100 with a more reliable effect to fix the external urethral orifice and prevents the periurethral tissue 013 from penetrating via the gap between the independent support legs 73, thereby eliminates the risk of contamination of the urinary catheter outer surface 12 by the periurethral tissue 013 that may be penetrated.

Figure 20:
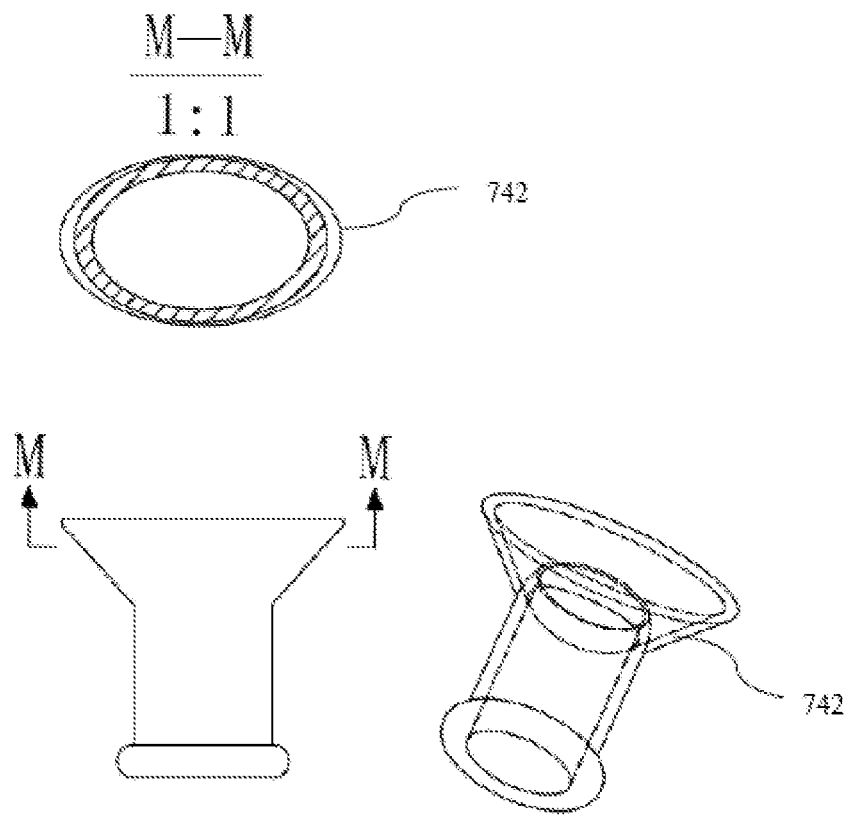
FIG. 20 is a schematic view of an oval support leg according to Embodiment 7 of the present utility model.

Embodiment 7: as shown in FIG. 20, the free end of an oval support leg 742 anatomically conforming to the shape of the body's periurethral tissue 013 is used, so as to minimize the resistance when pressing against the surface of the human body tissue and better prevent the periurethral tissue from contacting the urinary catheter outer surface 12.

Figure 21:
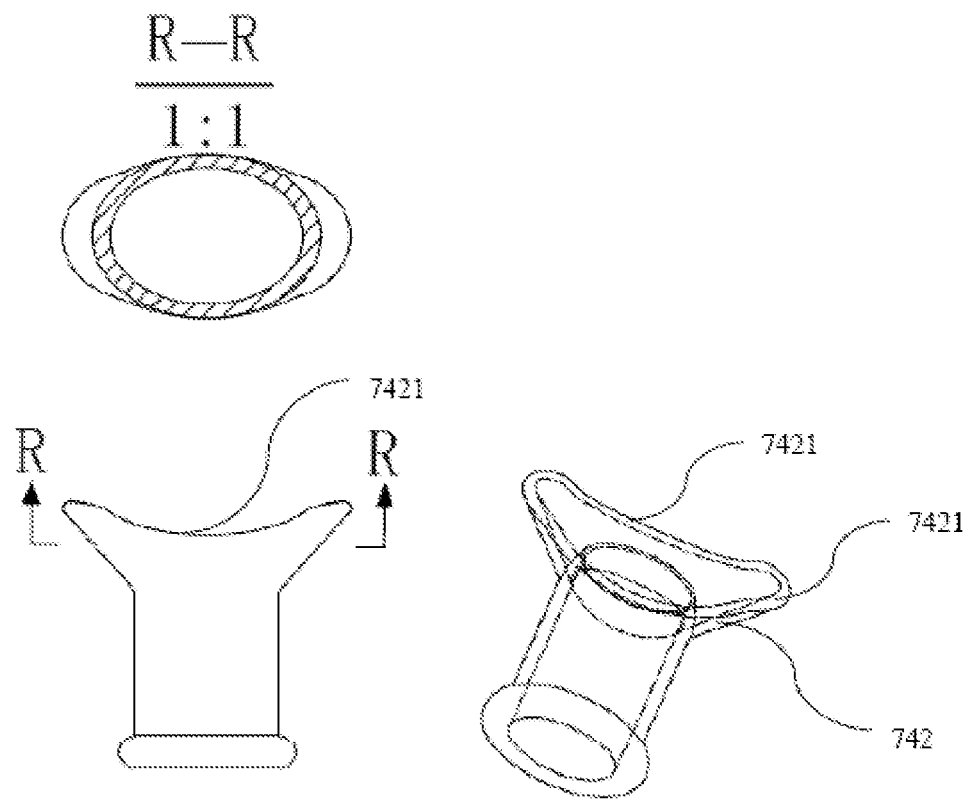
FIG. 21 is a schematic view of a three-dimensional end face oval support leg according to Embodiment 8 of the present utility model.

Embodiment 8: as shown in FIG. 21, in order to better conform to the shape of the periurethral tissue 013 at the target external urethral orifice 0100, the oval support leg free end 7421 of the oval support leg 742 may be a non-planar concave, which can be used for three-dimensional force application to better enlarge the external urethral orifice 0100; as an alternative to this embodiment, it is also possible to set a convex or a concave-convex combination shape according to the shape of the periurethral tissue 013 of the patient-specific external urethral orifice 0100.

Figure 22:
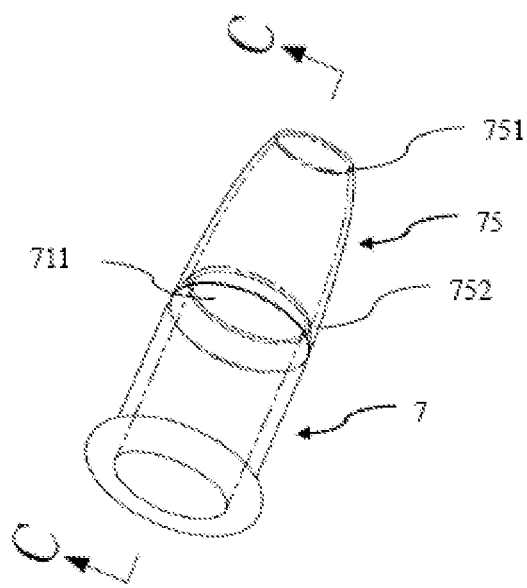
FIG. 22 is a schematic view of a urethral guide part according to Embodiment 9 of the present utility model.
Figure 23:
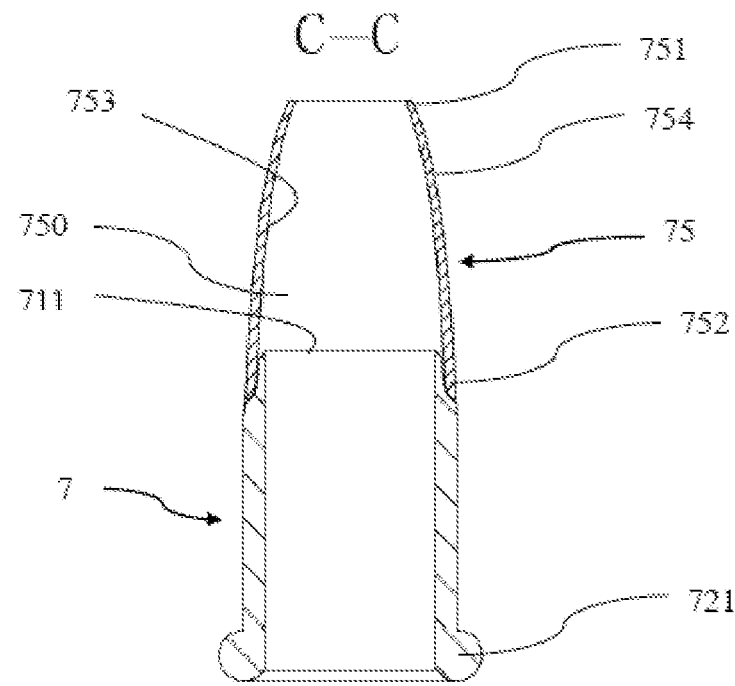
FIG. 23 is a plan view of a urethral guide part of FIG. 22 after section C-C is cut open in three dimensions according to Embodiment 9 of the present utility model.

Embodiment 9: as shown in FIG. 22 and FIG. 23, in order for the urinary catheter to better enter the urethra 01, a hollow and flexible urethral guide part 75 with both ends open capable of at least partially penetrating into the urethra 01 is provided on one side of the fixing part top end opening 711 of the fixing part 7, wherein, the urethral guide part 75 as a whole has a tapered shape with the guide part bottom end 752 tapering toward the guide part top end 751, and the guide part bottom end 752 is sleeved outside the fixing part top end opening 711 of the fixing part 7; when it is used, the guide part lateral surface 754 of the urethral guide part 75 comes in contact with the urethral intima 011, and the guide part medial surface 753 comes in contact with the urinary catheter outer surface 12 protruding from the fixing part top end opening 711 of the fixing part 7.

In some cases, such as undesirable patient posture or poor space position feeling of operators, even with the "US-guided adjacent placement" provided by the present utility model described above, although the urinary catheter tip 131 is easy to advance along the vertical urethral centerline 0101, it does not have a urinary catheter tip 13 of sufficient length to enter the urethra at the very beginning, so it cannot play the guiding role of the urethra 01 itself to the catheter inside it. The urethral intima 011 is made of a material softer than that of the catheter and cannot effectively correct possible deviations during the procedure, so it is difficult to ensure that the catheter tip centerline 1316 completely overlaps with the urethral centerline 0101. The most ideal way is to have a part, i.e. the urethral guide part 75, probing into a portion of the urethra in advance, with the urinary catheter tip end 131 advancing along this part to ensure that it is guided to the urethral centerline 0101, while avoiding damage to the urethral intima 011 caused by the urinary catheter tip end 131 due to the direction deviation, and the urinary catheter tip end does not directly press against the urethral intima 011 when the direction deviation occurs, but slides on the guide part medial surface 753.

Figure 24:
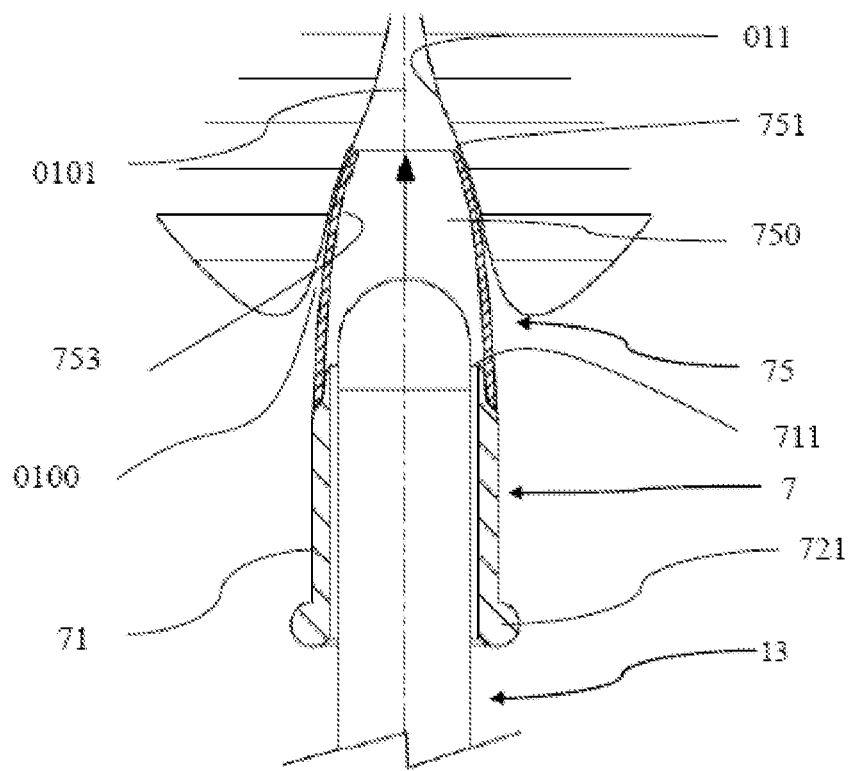
FIG. 24 is a schematic view of a urethral guide part when it is used according to Embodiment 9 of the present utility model.

When it is used, as shown in FIG. 24, the urinary catheter tip 13 enters the urethral guide part interior 750 from the fixing part top end opening 711 of the fixing part 7, slides forward along the guide part medial surface 753, extends out from the guide part top end 751 of the urethral guide part 75, partially enters the urethra and touches the urethral centerline 0101, continues to move forward in the direction of the bladder 0 along the vertical urethral centerline 0101 under the guidance of the urethra, thus achieving better docking with the urethra 01 and exerting the guiding role of the urethra 01, and adjusting the tilting angle of the fixing part body 71 at any time according to the resistance suffered in the advancing process, which further improves the accuracy and success rate of the urinary catheterization, and also further reduces possible injury to the urethral intima 011, with arrows in the figure indicating the direction of travel of the urinary catheter tip 13.

Figure 25:
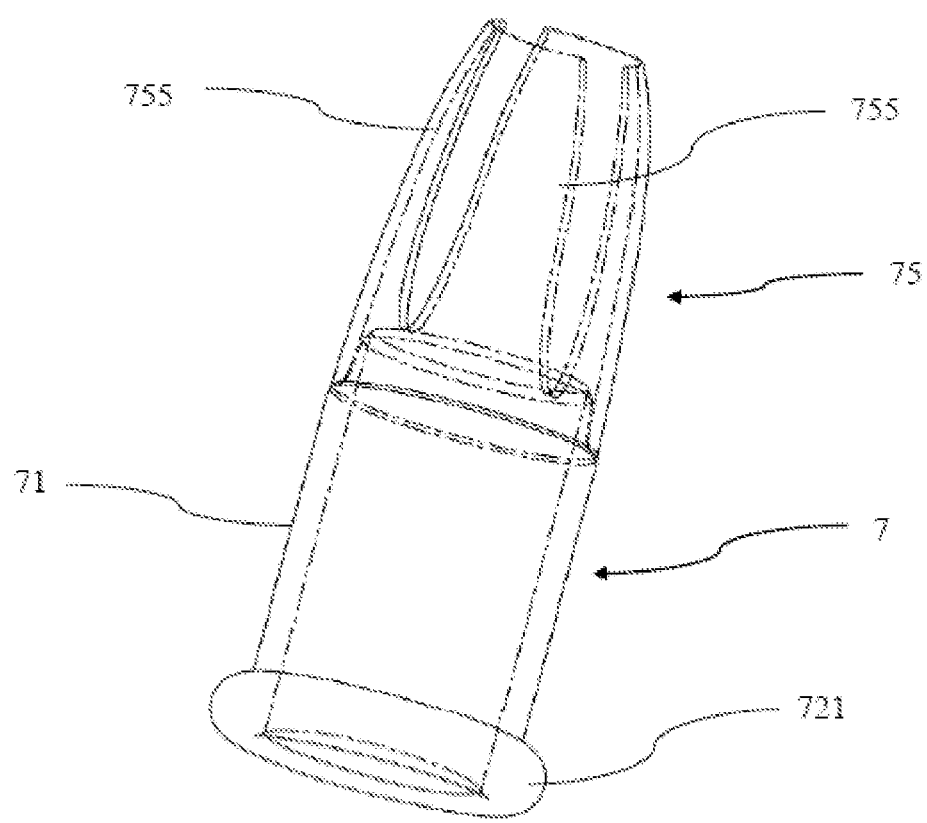
FIG. 25 is a schematic view of a valviform urethral guide part according to Embodiment 10 of the present utility model.

Embodiment 10: as shown in FIG. 25, the main body of the urethral guide part 75 connected to the fixing part 7 is composed of two guide valves 755, and the two guide valves 755 mostly separated in advance facilitate outward dilatation and deformation of the urinary catheter as it passes.

Figure 26:
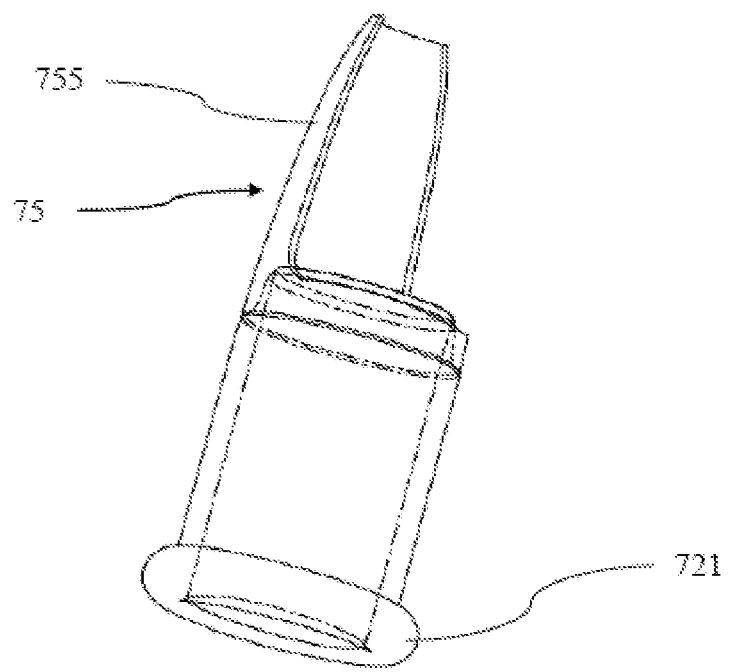
FIG. 26 is a schematic view of a single-valviform urethral guide part according to Embodiment 11 of the present utility model.

Embodiment 11: as shown in FIG. 26, the guide part 75 is provided with a guide valve 755, which is a conical shape bent inward as a whole. Larger deformation of the single guide valve 755 ensures more convenience for the catheter to dilate and deform outward as it passes.

Figure 27:
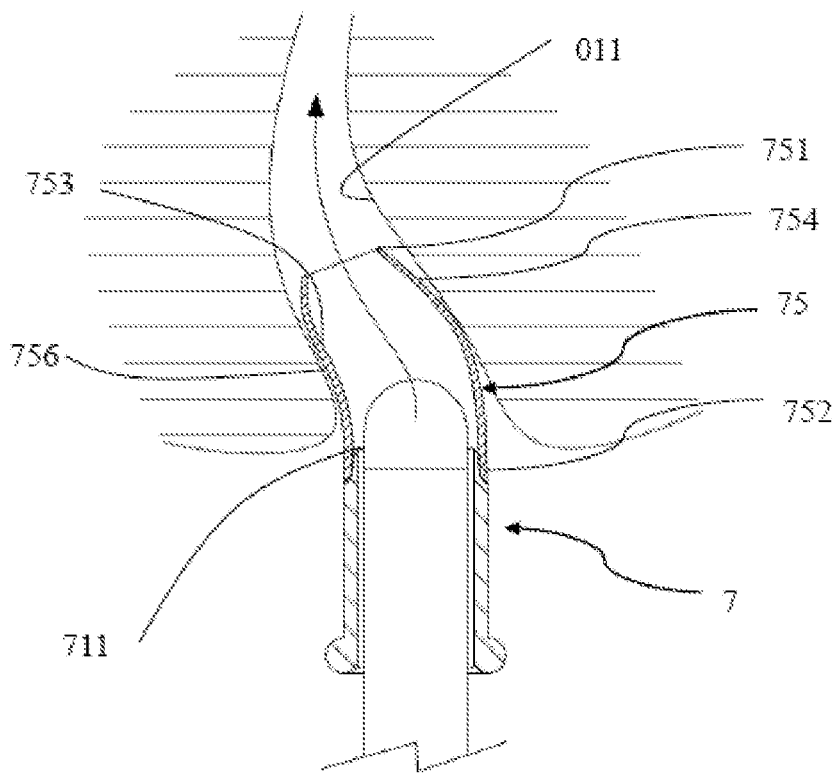
FIG. 27 is a schematic view of a curved urethral guide part according to Embodiment 12 of the present utility model.

Embodiment 12: as shown in FIG. 27, a curved urethral guide part 756 of taper shape as a whole tapers from the guide part bottom end 752 toward the guide part top end 751 and bends. The guide part bottom end 752 is designed to enter the curved urethra and sleeved outside the fixing part top end opening 711 of the fixing part 7. When it is used, the guide part lateral surface 754 of the curved urethral guide part 756 comes in contact with the curved urethral intima 011, and the curved guide part medial surface 753 comes in contact with the urinary catheter tip 13 extending from the fixing part top end opening 711 of the fixing part 7, with arrows in the figure indicates the curved travel route of the catheter.

Figure 28:
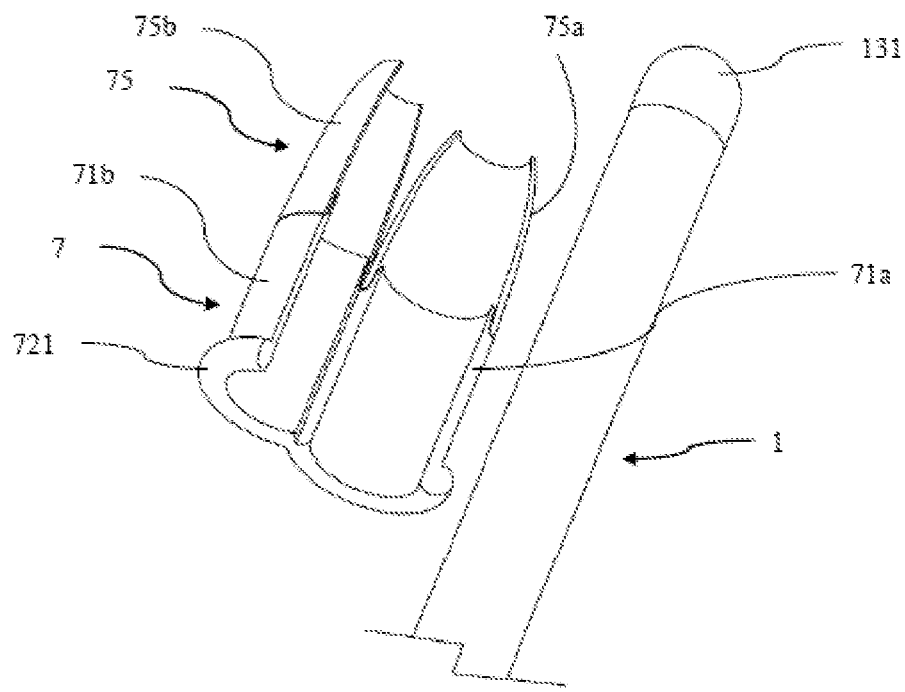
FIG. 28 is a schematic view of an openable and closable fixing part and a urethral guide part according to Embodiment 13 of the present utility model.

Embodiment 13: as shown in FIG. 28, in order to facilitate the separation of the fixing part 7 and the associated urethral guide part 75 from the catheter after the catheter is inserted, the fixing part 7 has a structure in which one side can be movably connected and the other side can be disconnected, that is, it can be opened and closed. The independent urethral guide parts 75a and 75b are respectively connected to the two main bodies 71a and 71b of the fixing part which are connected into a whole but can be opened and closed. When the catheter is used, the two sides are closed, and the catheter is restrained inside. When the catheter is inserted into the bladder, it is opened to separate it from the part of the catheter left outside.

Figure 29:
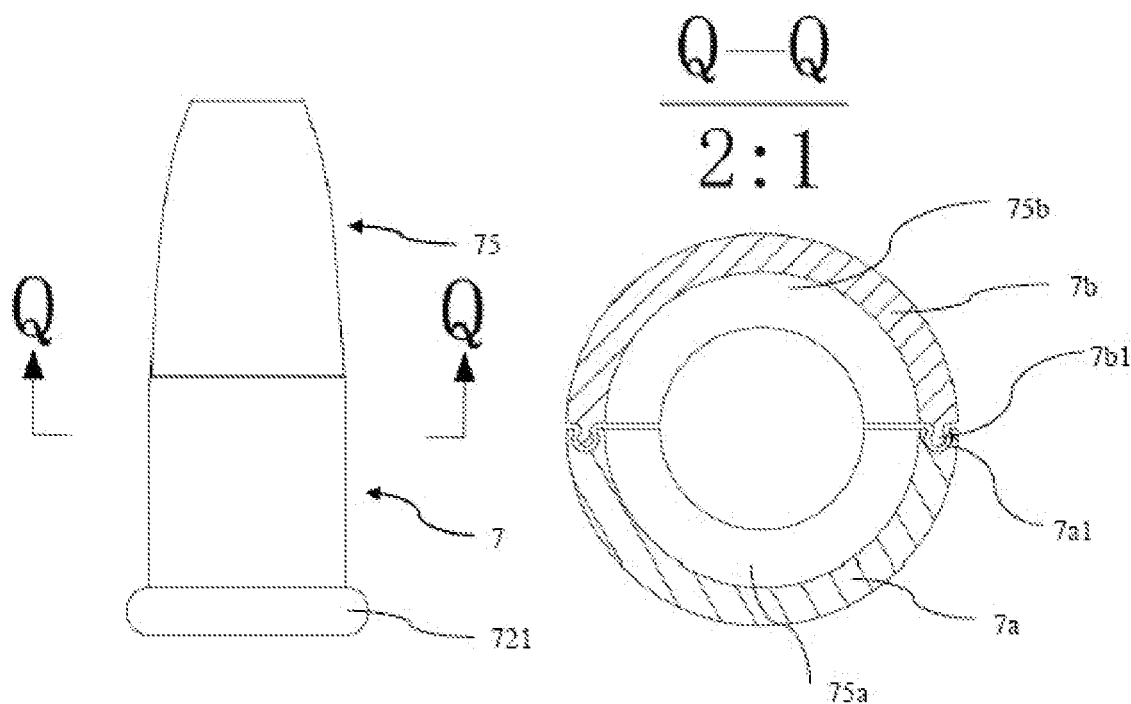
FIG. 29 is a schematic view of an openable and closable fixing part and a urethral guide part according to Embodiment 14 of the present utility model.

Embodiment 14: as shown in FIG. 29, another openable and closable design is that the fixing part 7 is composed of two independent parts 7a, 7b, in which, the independent urethral guide parts 75a, 75b are respectively connected with the independent fixing parts 7a, 7b, the side end face of the independent fixing part 7a is provided with a fixing part side end face groove 7a1, and the side end face of the independent fixing part 7b is provided with a fixing part side end face rib 7b1, which can be assembled in a sliding fit with each other or can be slid until separated.

Figure 30:
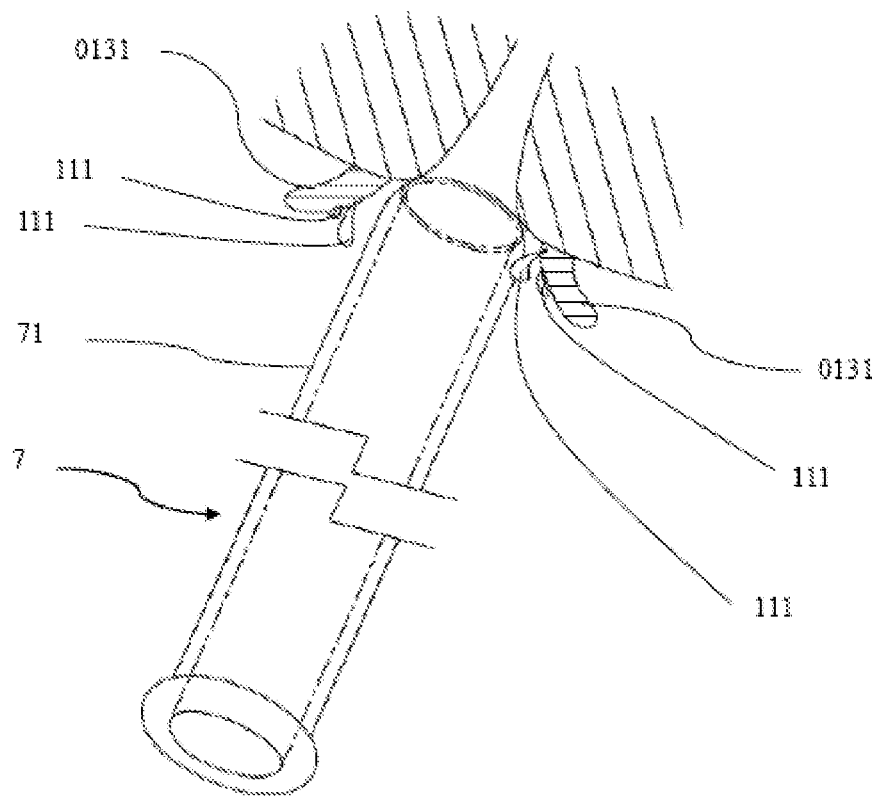
FIG. 30 is a schematic view of an extended fixing part according to Embodiment 15 of the present utility model.
Figure 31:
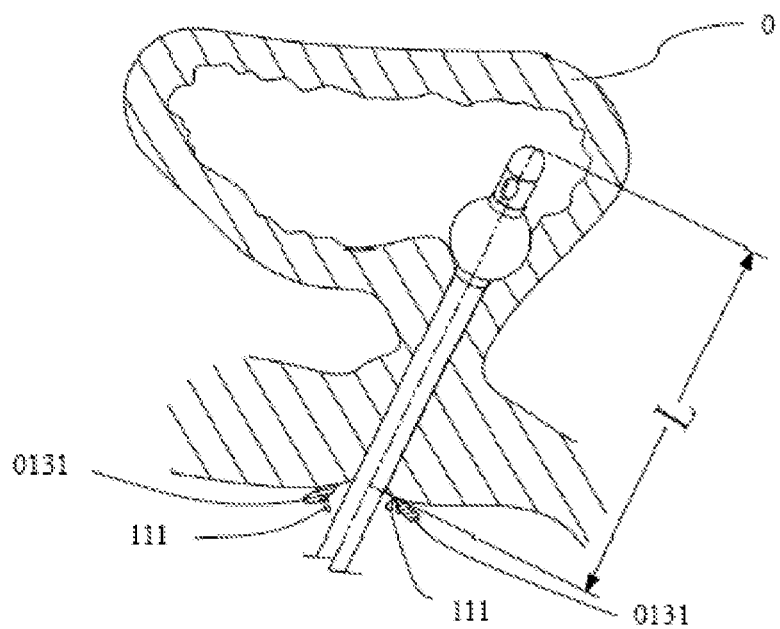
FIG. 31 is a schematic view of the urinary catheter entering the urethra and bladder in the extended fixing part according to Embodiment 15 of the present utility model.
Figure 32:
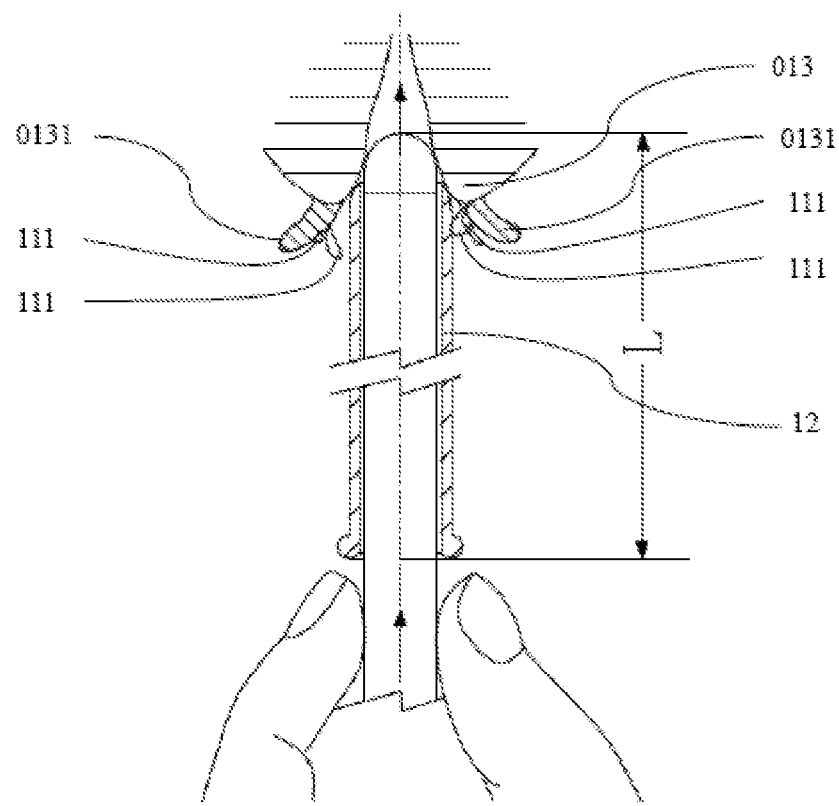
FIG. 32 is a schematic view of a fixing part guiding the movement of the urinary catheter therein according to Embodiment 15 of the present utility model.

Embodiment 15: as shown in FIG. 6, the traditional method of "non-guided suspended placement" of the catheter easily causes the contamination 111 on the periurethral tissue 013 to contact the urinary catheter outer surface 12, and brings the contamination 111 into the bladder cavity 00 to cause infection. In order to completely solve this problem, as shown in FIGS. 30 and 31, the fixing part body 71 of the fixing part 7 is extended, and the length of the catheter that can be accommodated in the extended fixing part 7 is greater than or equal to the length L of the catheter that is located in the bladder 0 and urethra 01 when the catheter is retained. Such design of lengthening the fixing part body 71 of the fixing part 7 ensures that the urinary catheter part entering the bladder and the urethra does not contact with the contamination 111 on periurethral tissue 013 during the insertion of the urinary catheter, and completely eliminates the risk of urinary tract infection caused by the periurethral tissue 013 contaminating the urinary catheter outer surface 12, with arrows in the figures indicating the direction of travel of the urinary catheter. When the existing technique of lubricating the coating on the urinary catheter outer surface 12 is applied, lubricating substances such as chitosan, sodium hyaluronate and the like can be coated on the urinary catheter outer surface 12 greater than this length L.

Figure 33:
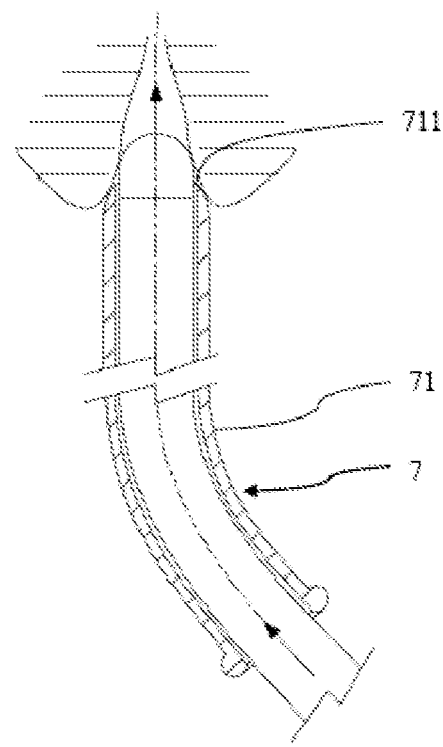
FIG. 33 is a schematic view of a curved fixing part according to Embodiment 16 of the present utility model.

Embodiment 16: as shown in FIG. 33, another consideration is that in order to adapt to the stricture, deflection of the external urethral orifice and even curvature of the urethra of some patients, a portion of the fixing part top end opening 711 of the fixing part 7 is at a certain angle to the fixing part body 71 from the point of view of easy operation and reduction of injury. As an alternative to the idea of this embodiment, the urethral guide part 75 may also be designed at an angle to the fixing part top end opening 711 of the fixing part 7. The fixing part top end opening 711 of the fixing part 7 and the fixing part body 71 may also be a steerable connection including a bellows, the said steerable connection being a connection with an adjustable connection angle, and the arrows in the figure indicates the direction of travel of the urinary catheter.

Figure 34A:
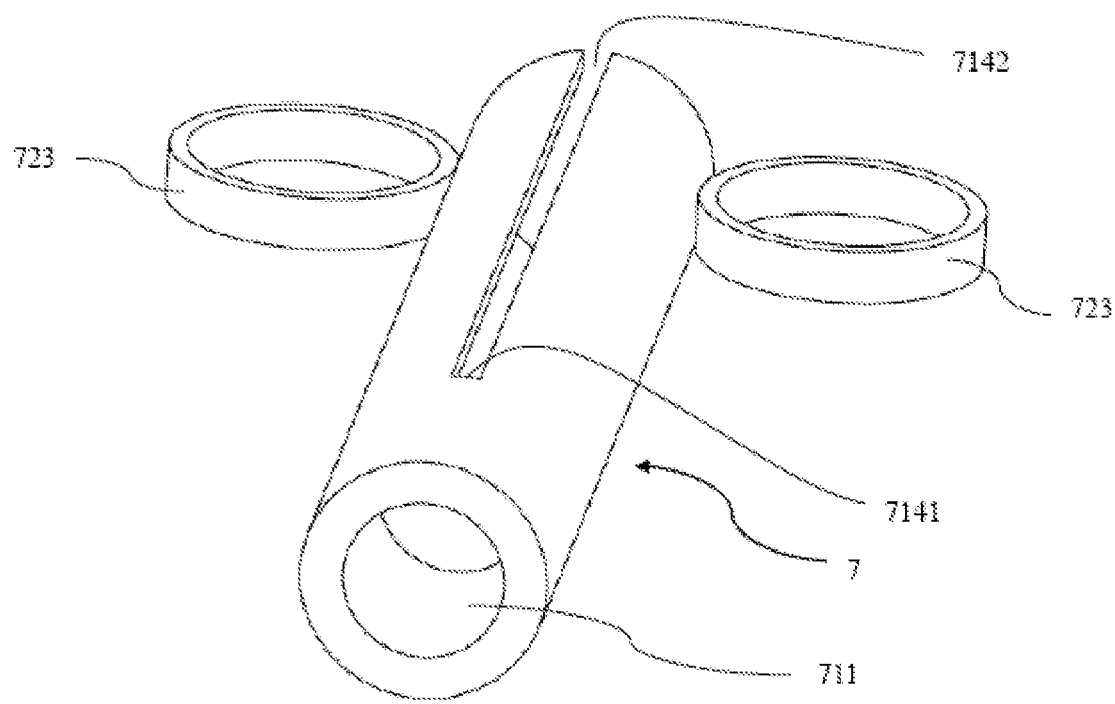
FIG. 34*a* is a schematic view of a fixing part according to Embodiment 17 of the present utility model.
Figure 34B:
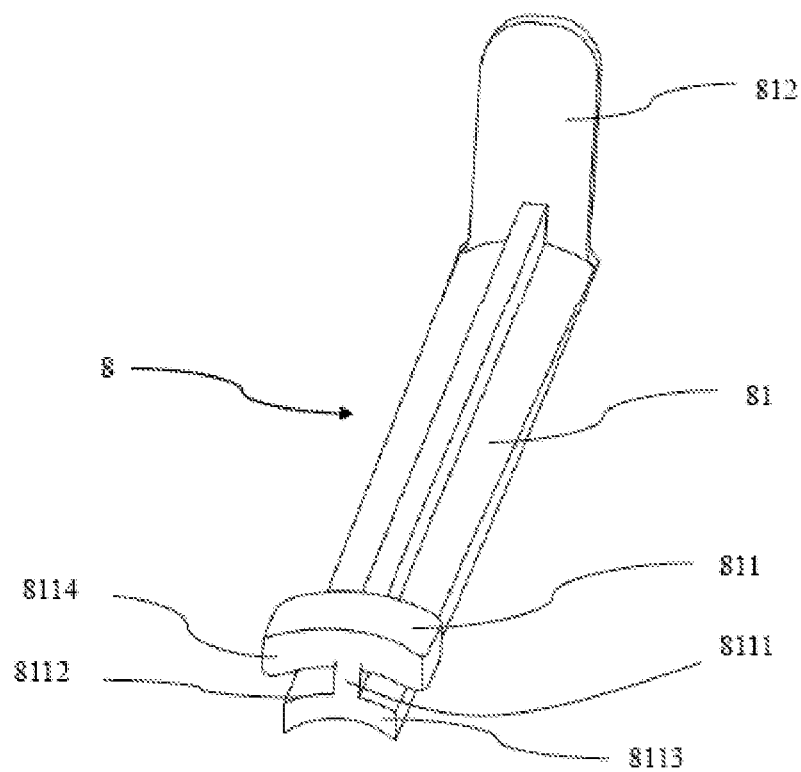
FIG. 34*b* is a schematic view of a driving part according to Embodiment 17 of the present utility model.
Figure 34C:
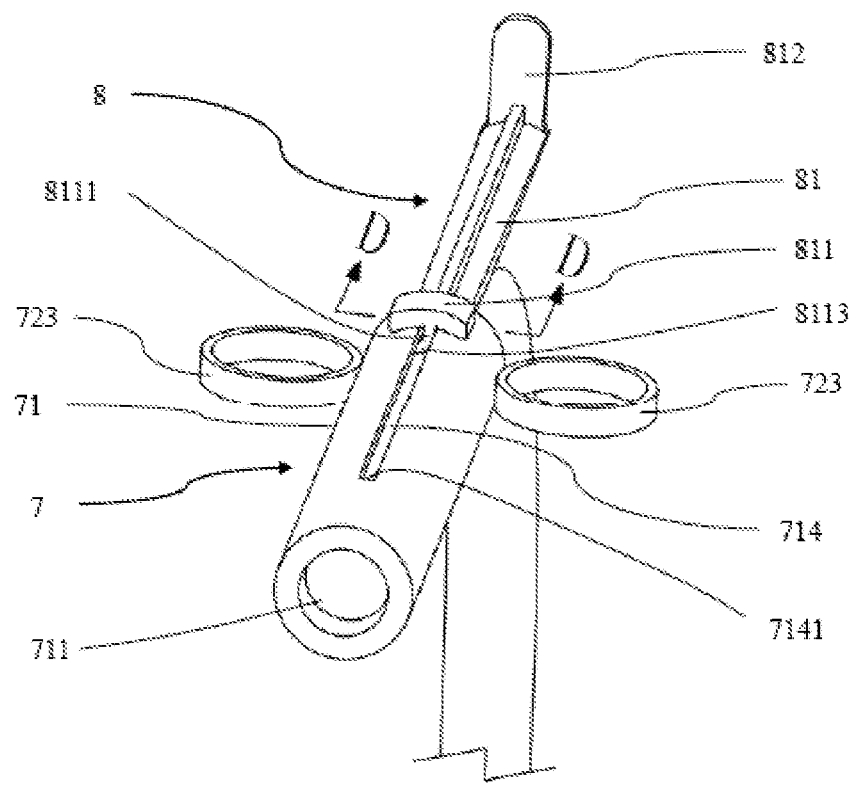
FIG. 34*c* is a schematic view of Embodiment 17 of the present utility model.
Figure 35A:
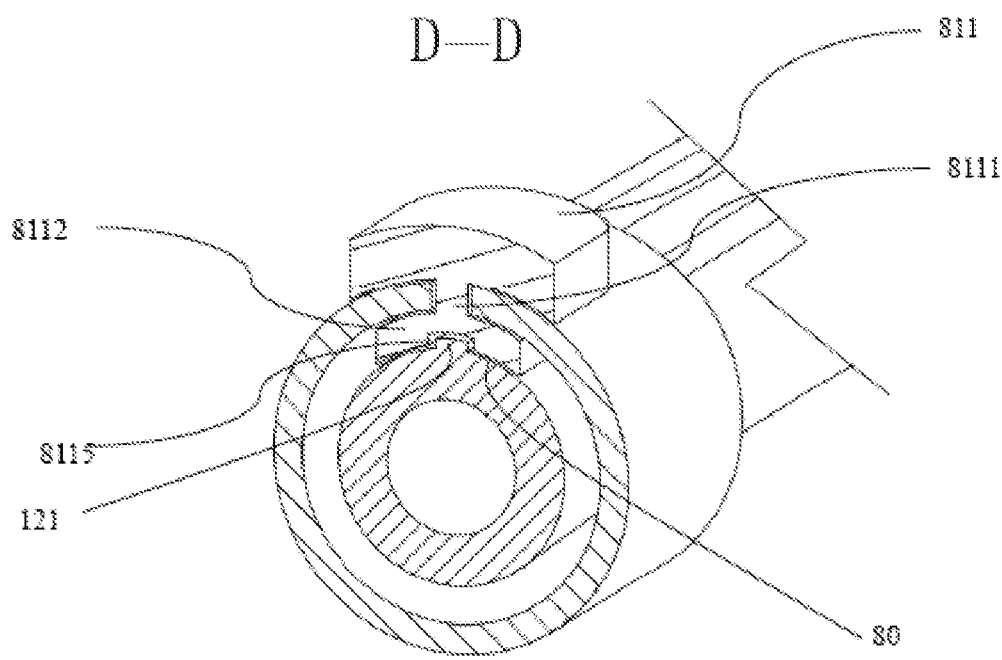
FIG. 35*a* is a perspective view of a driving part of FIG. 34*c* driving the urinary catheter after section D-D is cut open in three dimensions according to Embodiment 17 of the present utility model.
Figure 35B:
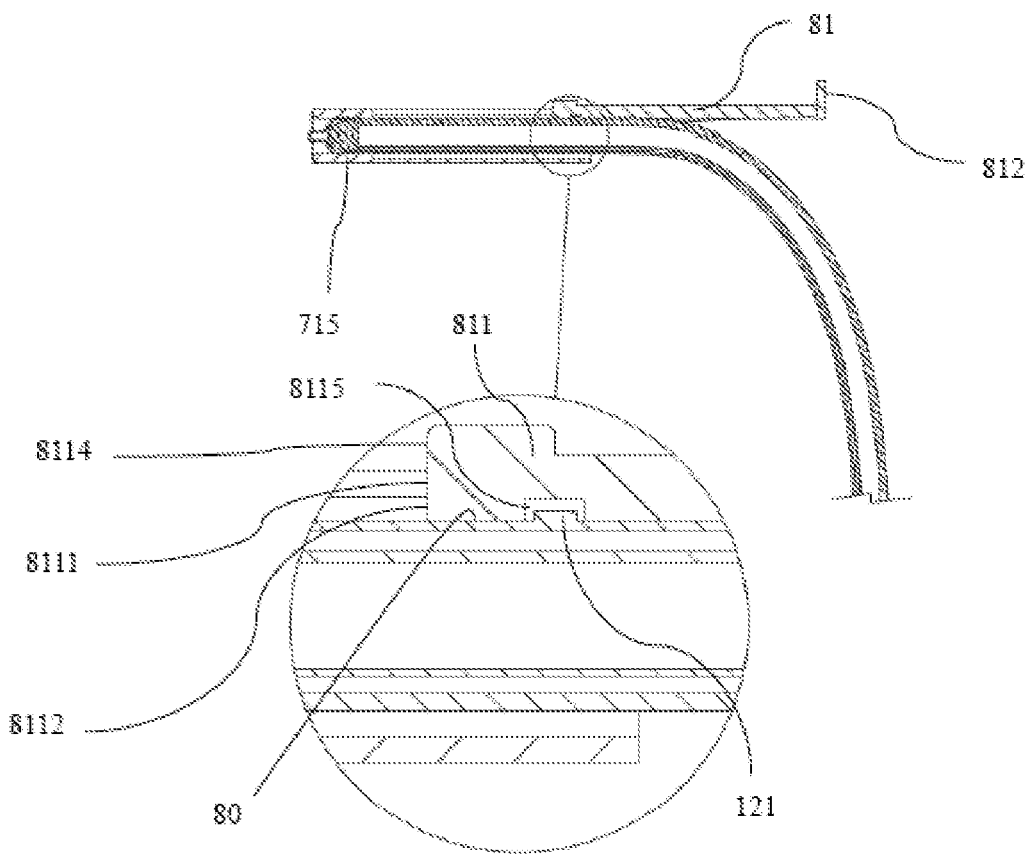
FIG. 35*b* is a structural schematic view of a driving part driving the urinary catheter according to Embodiment 17 of the present utility model.

Embodiment 17: as shown in FIG. 34a, in order to better insert the urinary catheter 1, especially to facilitate one-handed operation, the side wall of the fixing part body 71 of the fixing part 7 is provided with an elongated fixing part body through slot 714 penetrating inside and outside, in which, the through slot top end 7142 of the fixing part body through slot 714 is opened to the outside, and the through slot bottom end 7141 of the fixing part body through slot 714 is located close to the fixing part top end opening 711 of the fixing part 7. As shown in FIG. 34b, it is also provided with a catheter driving part 8 with a rod-shaped main body that is sleeved with the fixing part body 71 of the fixing part 7. One end of the driving part rod-shaped body 81 is a driving part tip 811 that is sleeved with the fixing part body 71 of the fixing part 7, and the driving part tip 811 is slidably fit with the fixing part body 71. Specifically, the driving part tip 11 extends out a portion 8111, the width of which is smaller than that of the fixing part body through slot 714, and the portion 8111 that extends out of the driving part tip 811 is inserted via the open through slot top end 7141 of the fixing part body through slot 714 on the fixing part body 71 of the fixing part 7 and slid fit with the fixing part body 71 of the fixing part 7, with the travel ended at the through slot bottom end 7141 of the fixing part body through slot 714 and such travel is greater than or equal to the sum L of the lengths of the urinary catheter located in the bladder 0 and urethra 01 when the urinary catheter is retained. The portion 8111 of the driving part tip 811 of the driving part 8 fit into the fixing part body through slot 714 is connected with an arc-shaped anti-prolapse portion 8112, the width of which is larger than that of the fixing part body through slot 714; the driving part tip top end face 8114 and the anti-prolapse portion top end face 8113 of the driving part tip 811 face the direction of the fixing part top end opening 711 of the fixing part 7. The assembly of the fixing part 7 and the driving part 8 is shown in FIG. 34c. As shown in FIGS. 35a and 35b, the driving part tip inner surface 80 of the anti-prolapse portion 8112 of the driving part tip 811 of the driving part 8 has at least one concave driving part force application part 8115, and the catheter wall at the corresponding position is provided with a convex catheter wall force bearing part 121; the driving part tail 812 of the driving part 8 is perpendicular to the driving part rod-shaped body 81 to facilitate the operation of a person's finger. In practice, the driving part force application part 8115 may also be a partial convex or annular boss, while the catheter wall part force bearing part 121 is a recess matched with the force application part. In order to ensure that the urinary catheter 1 can be guided reliably and accurately during its advancement in the fixing part 7, a fixing part top end guide portion 715 with an inner diameter slightly larger than the outer diameter of the catheter is provided inside the fixing part top end opening 711 adjacent to the fixing part 7. In use, when an operator use his/her two fingers, usually the index finger and the middle finger, to hold the fixing part finger ring 723 on the fixing part 7, the thumb of the same hand pushes the driving part tail 812 and the driving part 8 moves in the direction of the external urethral orifice 0100, the catheter is also driven by the driving part to move synchronously into the urethra 01 through the fixing part top end guide portion 715 at the fixing part top end opening 711 of the fixing part 7. When the driving part 8 moves in the opposite direction to the external urethral orifice 0100, the urinary catheter can be driven out of the urethra 01.

As an alternative to this embodiment, the catheter driving part body 81 may also be a hollow rod shape or a tube shape that accommodates the catheter 1, or may be a semi-arc rod shape or a bent rod shape that conforms to the bent fixing part.

Figure 36:
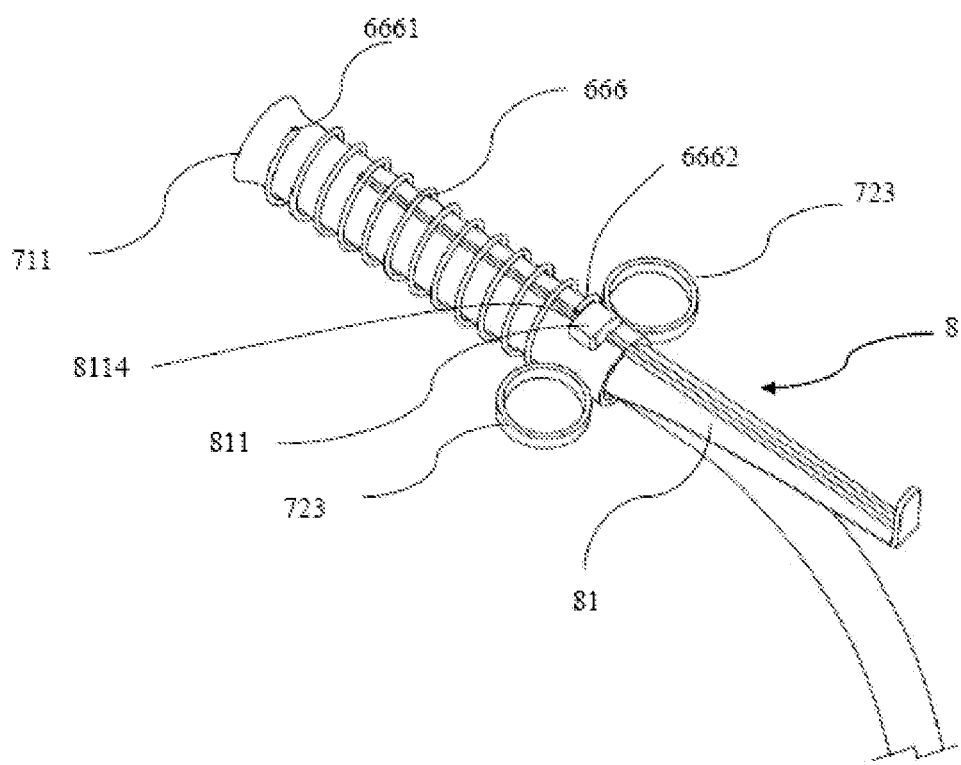
FIG. 36 is a schematic view of an external return spring according to Embodiment 18 of the present utility model.

Embodiment 18: as shown in FIG. 36, on the basis of embodiment 17 it further comprises a return spring 666, which is sleeved between the vicinity of the fixing part top end opening 711 of the fixing part 7 and the driving part 8, especially the driving part tip 811, to prevent the driving part 8 from moving toward the top end of the fixing part 7.

The stationary end 6661 of the return spring 666 is located near the fixing part top end opening 711 of the fixing part 7, and its movable end 6662 abuts against the driving part tip top end face 8114 of the driving part tip 811 of the urinary catheter driving part 8.

If the urinary catheter encounters resistance when advancing in the urethra, it may be due to urethral stricture and/or curvature. Considering forced advancement will surely damage the urethra at this time, stop applying force, then the return spring 666 can partially push off the driving part 8 to drive part of the urinary catheter out of the urethra. Adjust the direction or take other measures such as adding lubricating oil and then operate again.

Figure 37:
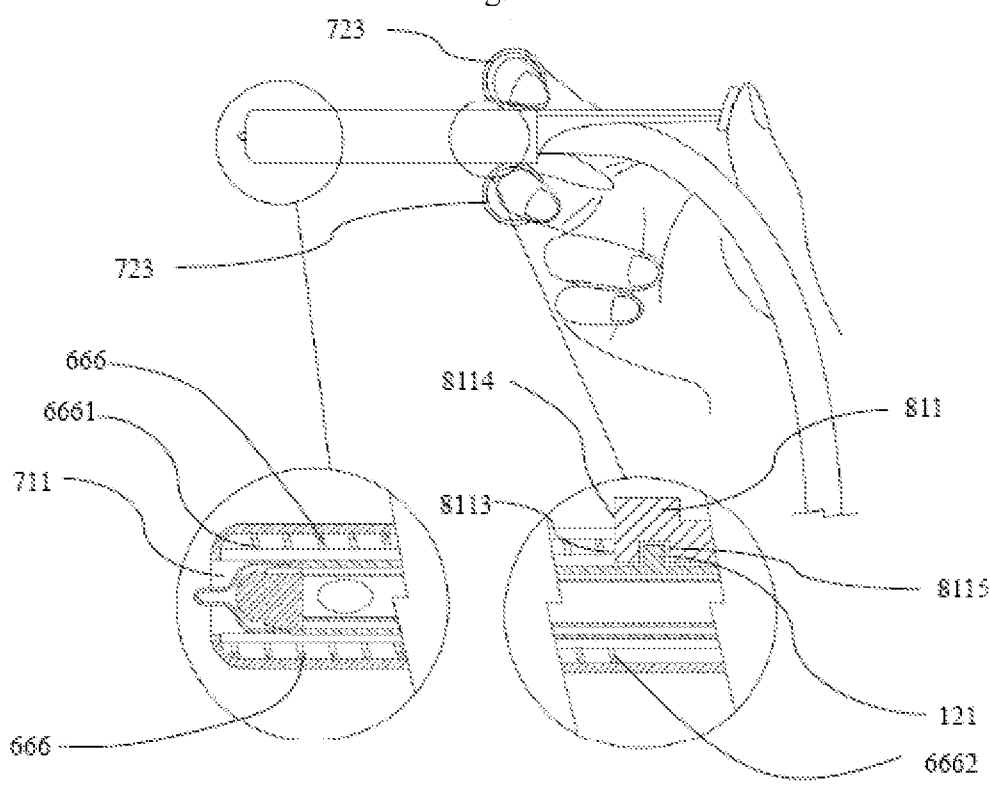
FIG. 37 is a schematic view of a built-in return spring according to Embodiment 19 of the present utility model.

Embodiment 19: as shown in FIG. 37, the return spring 666 is internally sleeved in the fixing part cylindrical hollow 70 of the fixing part 7, and the movable end 6662 abuts against the anti-prolapse portion top end face 8113 of the anti-prolapse portion 8112 of the driving part tip 811 of the driving part 8.

Figure 38:
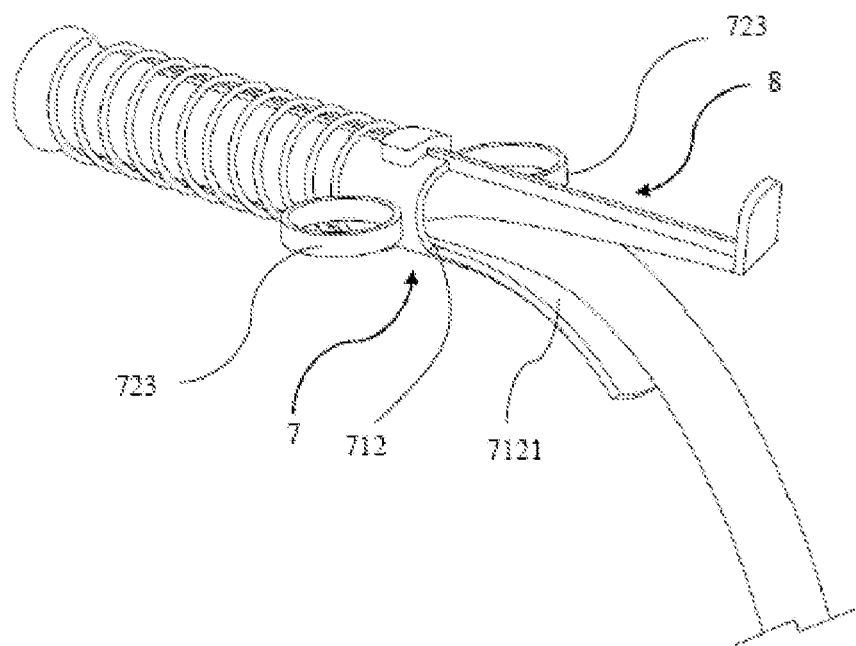
FIG. 38 is a schematic view of a guide slot according to Embodiment 20 of the present utility model.

Embodiment 20: as shown in FIG. 38, a slightly curved fixing part guide groove 7121 extends from the fixing part tail end opening 712 of the fixing part 7. When the catheter driving part 8 drives the catheter to travel into the fixing part 7, the catheter slides in the slightly curved fixing part guide groove 7121 to avoid additional pushing resistance caused by serious falling and bending of the catheter route due to gravity.

Figure 39:
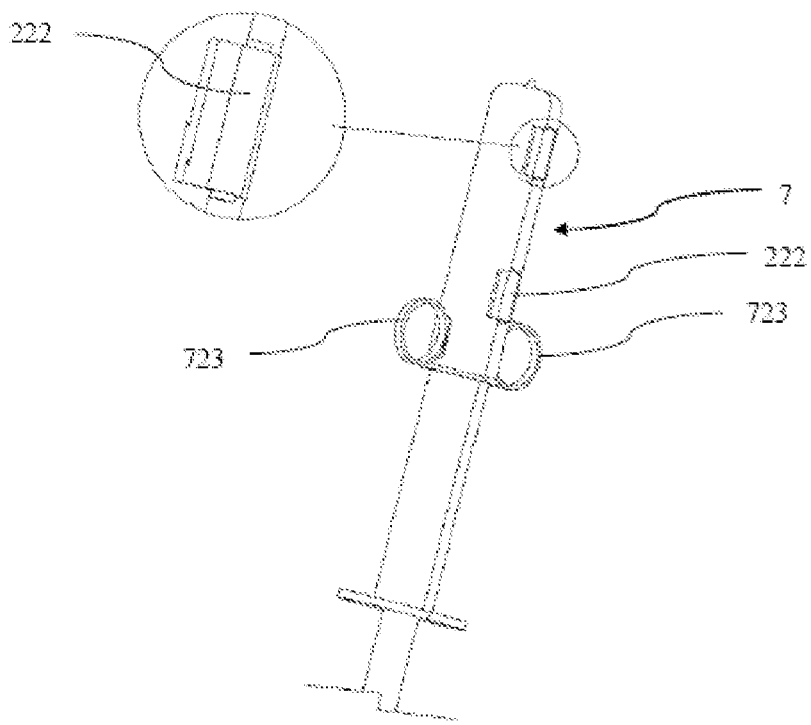
FIG. 39 is a schematic view of an openable and closable part according to Embodiment 21 of the present utility model.

Embodiment 21: as shown in FIG. 39, the fixing part 7 is composed of two parts, which are connected by hinges 222 and opened and closed after the urethral catheterization procedure is completed to separate the fixing part 7 from the urinary catheter 1.

Figure 40:
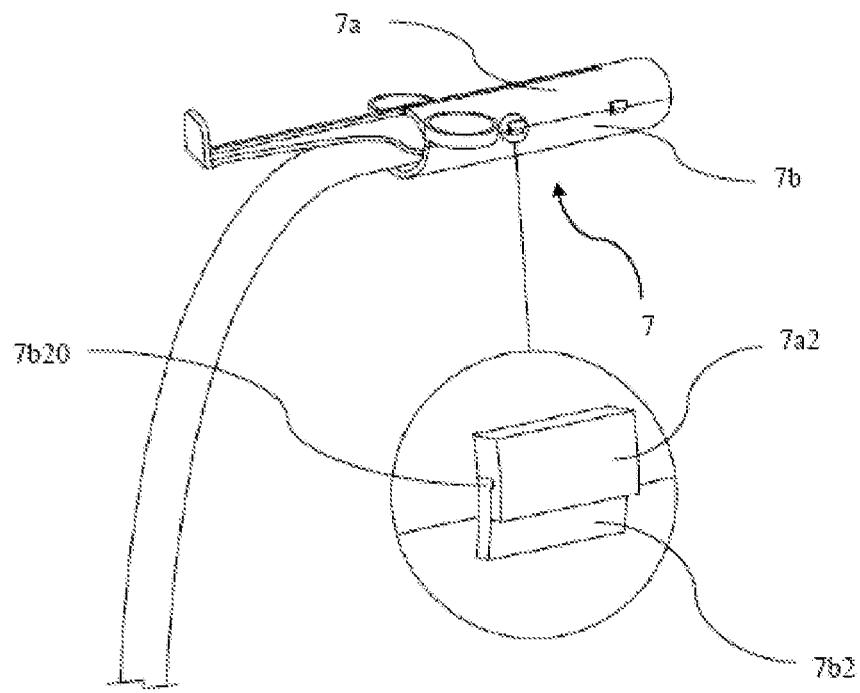
FIG. 40 is a schematic view of an openable and closable part according to Embodiment 22 of the present utility model.

Embodiment 22: as shown in FIG. 40, the fixing part 7 is composed of two independent parts 7a, 7b, in which two connecting parts 7a2 are respectively arranged on both sides of the independent fixing part 7a, and two connecting members 7b2 are also respectively arranged on both sides of the independent fixing member 7b2. A weak snap interference fit is formed between the connecting parts 7a2, 7b2, the two independent fixing parts 7a, 7b are forcibly engaged with each other, and the connecting part boss 7b2 on the connecting part 7b2 is tightly fit into a groove at a corresponding position on the connecting part 7a2. When it is used, the independent fixing parts 7a, 7b are matched and connected into a whole, and the two independent fixing parts 7a and 7b can be separated by holding them by hand with a little force after use.

Figure 41:
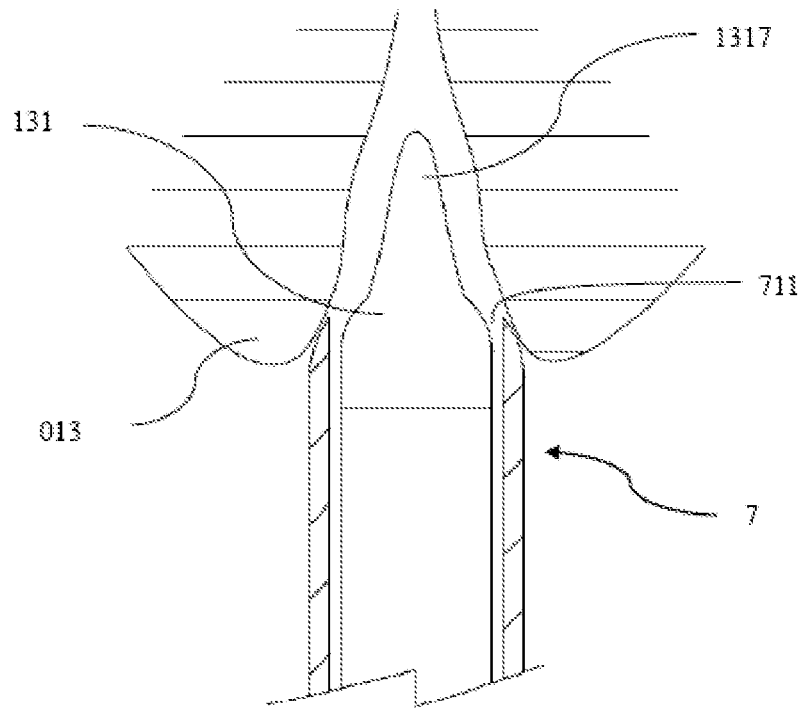
FIG. 41 is a structural schematic view of a urinary catheter tip according to Embodiment 23 of the present utility model.

Embodiment 23: a urethral guide structure as shown in FIG. 41 is that the catheter tip end 131 extends conically outward, and the urinary catheter tip end conical extension part 1317 extends from the fixing part top end opening 711 of the fixing part 7. The urinary catheter tip end conical extension part 1317 of the urinary catheter tip end 131 can be first inserted into the urethra when in use, to guide the urinary catheter tip 13 to move forward along the urethral centerline 0101, playing a similar role to the urethral guide part 75 as shown in FIG. 23, and can be used independently from the urethral guide part 75 or in conjunction with the previously-mentioned urethral guide part 75.

Figure 42:
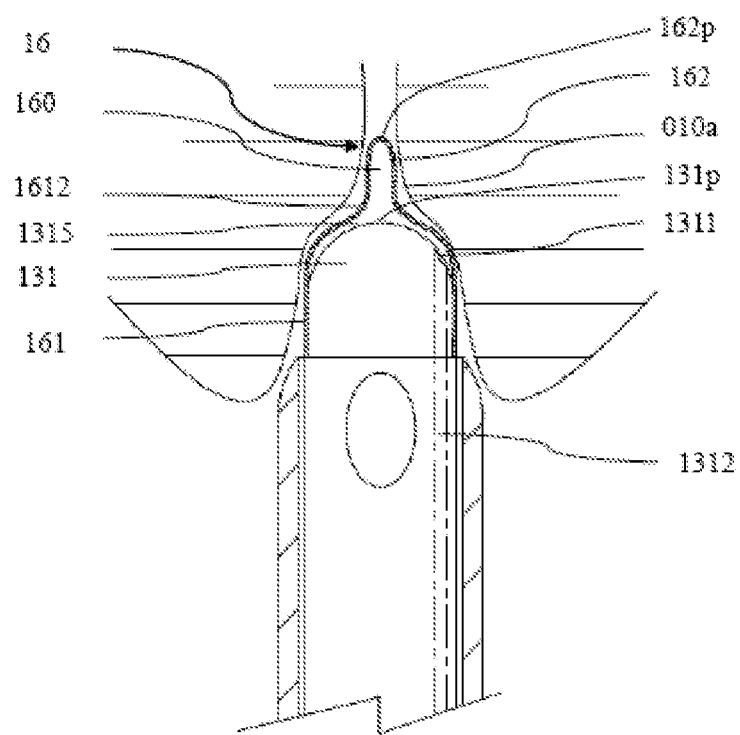
FIG. 42 is a structural schematic view of a thin segment of a urinary catheter tip according to Embodiment 24 of the present utility model.
Figure 43:
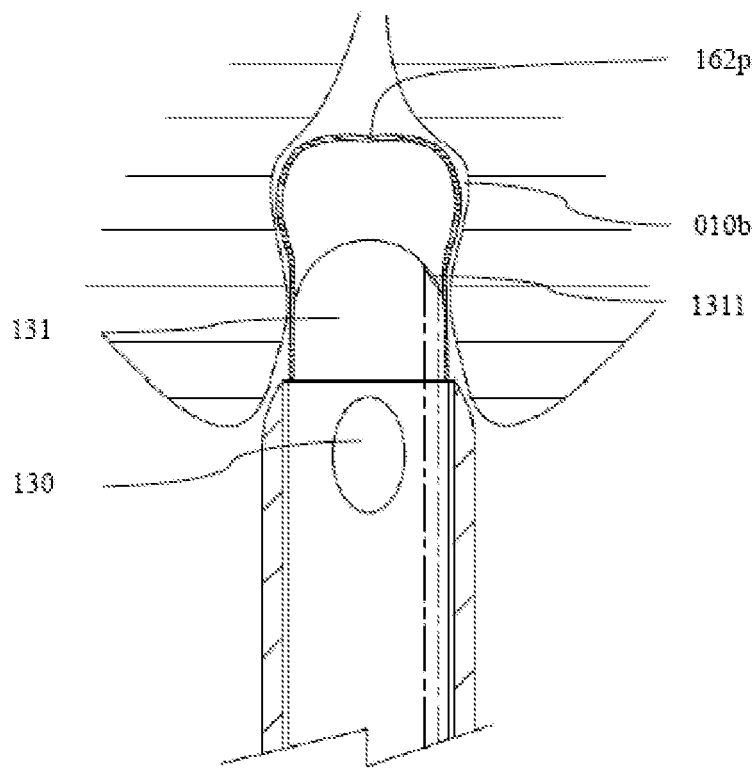
FIG. 43 is a schematic view of a dilated thin segment of a urinary catheter tip according to Embodiment 24 of the present utility model.
Figure 44:
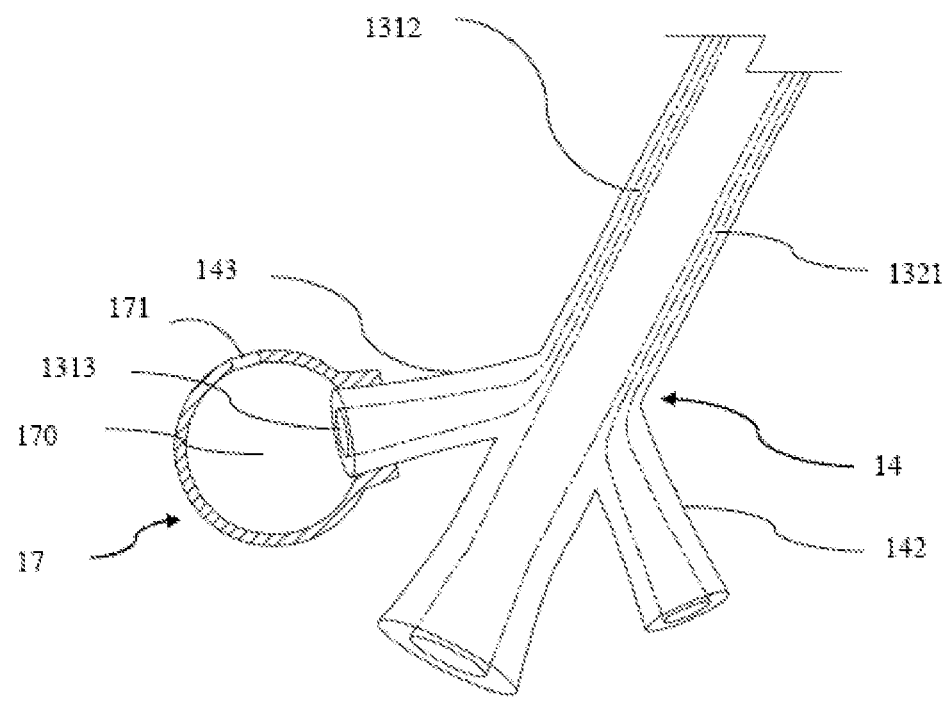
FIG. 44 is a structural schematic view of an elastic balloon of a urinary catheter according to Embodiment 24 of the present utility model.

Embodiment 24: as shown in FIGS. 42, 43 and 44, the outer surface of the urinary catheter tip end 131 is connected with a nipple-shaped flexible and hollow thin segment 16, and the hollow inside the thin segment 16 is a thin segment inner cavity 160, which may be without air or volume, but the thin segment inner cavity 160 may be enlarged after filled with fluid. One side of the thin segment 16 connected with the outer surface of the urinary catheter tip end 131 is a thin segment bottom 161 and the other side is a thin segment top 162; a portion of the thin segment bottom 161 is connected with the outer surface of the urinary catheter tip end 131 and is a connecting part of the thin segment, and the rest part including the thin segment top 162 is the thin segment dilatable part 1612; the thin segment inner cavity 160 is specifically formed by the inner surface of the thin segment dilatable part 1612 and the part of the urinary catheter tip end 131 whose outer surface is covered by the thin segment dilatable part 1612; the urinary catheter thin segment top 162 is closed to the outside by the blind end, and the average outer diameter of the part between the thin segment top farthest point 162p and the urinary catheter tip end farthest point 131p is smaller than the maximum outer diameter of the urinary catheter tip end 131; the thin segment inner cavity 160 is connected to the outside through at least one route on the urinary catheter wall, i.e., the thin segment inner cavity route 1312, which has at least one thin segment inner cavity route inner opening 1311 connecting with the thin segment inner cavity 160 and at least one thin segment cavity route outer opening 1313 connecting with outside space at the urinary catheter tail 14, and the thin segment inner cavity route outer opening 1313 in this embodiment is located on the filling collateral branch 143 of the thin segment of the urinary catheter tail 14.

When the catheter travels in the urethra and encounters a stricture, the catheter tip end 131 having a larger outer diameter cannot pass through, while the thin segment 16 having a smaller outer diameter, especially the thin segment top 162, can enter the urethral intima 010a of the stricture without causing damage to the urethra or the extent of damage is the lowest. At this time, stop advancing the urinary catheter, and as shown in FIG. 44, press the elastic balloon 17 on the filling collateral branch 143 of the thin segment to fill a certain volume of air and/or liquid at certain pressure into the thin segment inner cavity 160 through the thin segment inner cavity route 1312, as shown in FIG. 43, so that the thin segment 16 is inflated and maintained for a certain period of time, and the thrust generated by inflation is vertically applied on the urethral intima 011 at the stricture to dilate the urethra, and then the elastic balloon 17 is slackened and the elastic restoring force of the elastic balloon 17 itself sucks out the air and/or liquid in the thin segment inner cavity 160. After the dilatation of the thin segment 16 is relieved, continue to push the catheter forward and the urinary catheter tip end is easy to pass through the dilated urethral inner cavity 010b of the urethral portion, and on the premise of not damaging the urethra, push the catheter smoothly toward the direction of the bladder 0; continue to move forward and repeat the filling process of the above-mentioned thin segment 16 in case of recurrence of stricture until the catheter 1 is successfully inserted.

The elastic balloon inner cavity 170 may be filled with sterile water, glycerin and other liquid substances in advance.

The elastic balloon 17 used for filling the thin-section inner cavity 160 is provided with at least one elastic balloon external opening 171 which can be covered by fingers. The air in the elastic balloon inner cavity 170 is connected with the outside through this opening. When it is used, press the elastic balloon 17 while covering the elastic balloon external opening 171 with fingers. Since the elastic balloon external opening 171 is closed by fingers, the air in the elastic balloon inner cavity 170 is pressed to the thin segment inner cavity 160 through the thin segment inner cavity route 1312 and inflated to enlarge the strictured urethra. The elastic balloon 17 may be restored if the pressing is stopped, and the air entering the thin segment inner cavity 160 will be sucked back into the elastic balloon inner cavity 170, or the air entering the thin segment inner cavity 160 will be pushed back into the elastic balloon inner cavity 170 due to the elastic restoring force of the thin segment 16, or the finger's closure of the elastic balloon external opening 171 will be released, so that the air in the elastic balloon inner cavity 170 will be connected with the outside, and finally the thin segment 16 will recover from the dilated state. However, due to the presence of the elastic balloon external opening 171 during indwelling of the urinary catheter, when the elastic balloon 17 is pressed due to involuntary movement of the lower limbs or local medical care operation, the air and/or liquid in the elastic balloon inner cavity 170 can flow out of the elastic balloon external opening 171, thus avoiding possible stimulation of the bladder intima by the dilatation of the thin segment located in the bladder at this time.

Figure 5:
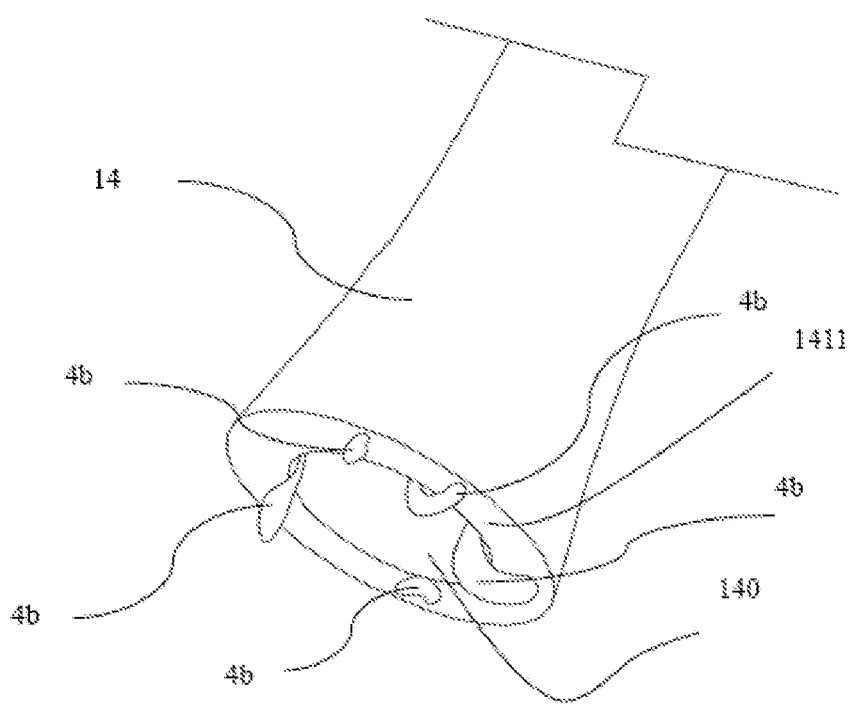
FIG. 5 is a schematic view of an end face of a urine outlet of a urinary catheter contaminated by urine outflow.
Figure 45A:
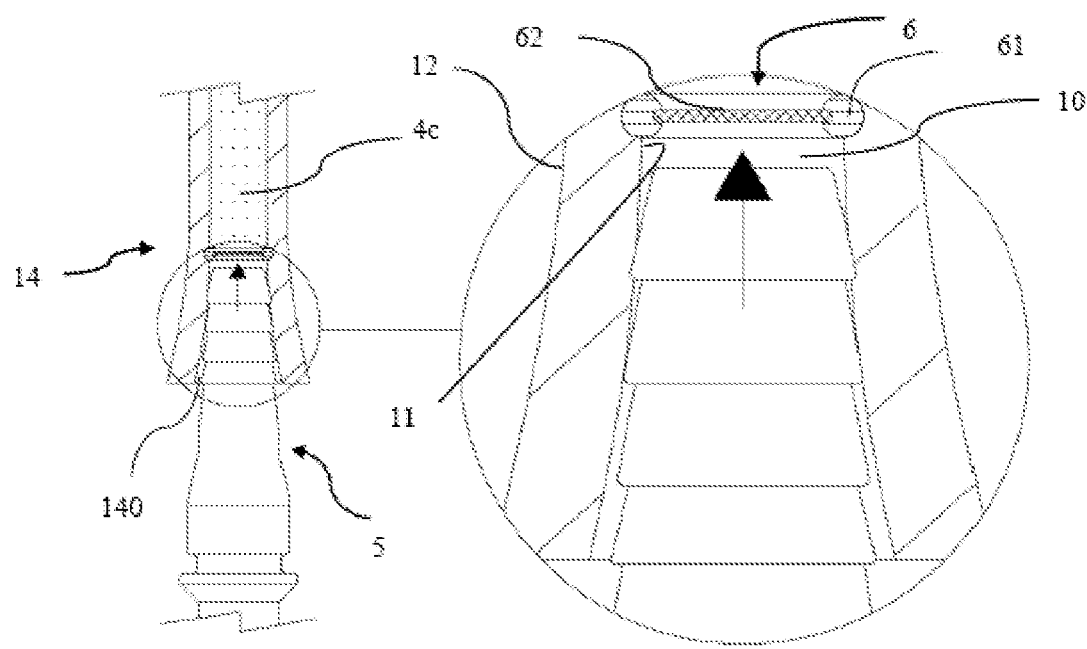
FIG. 45a is a structural schematic view of a urinary catheter tail according to Embodiment 25 of the present utility model.
Figure 45B:
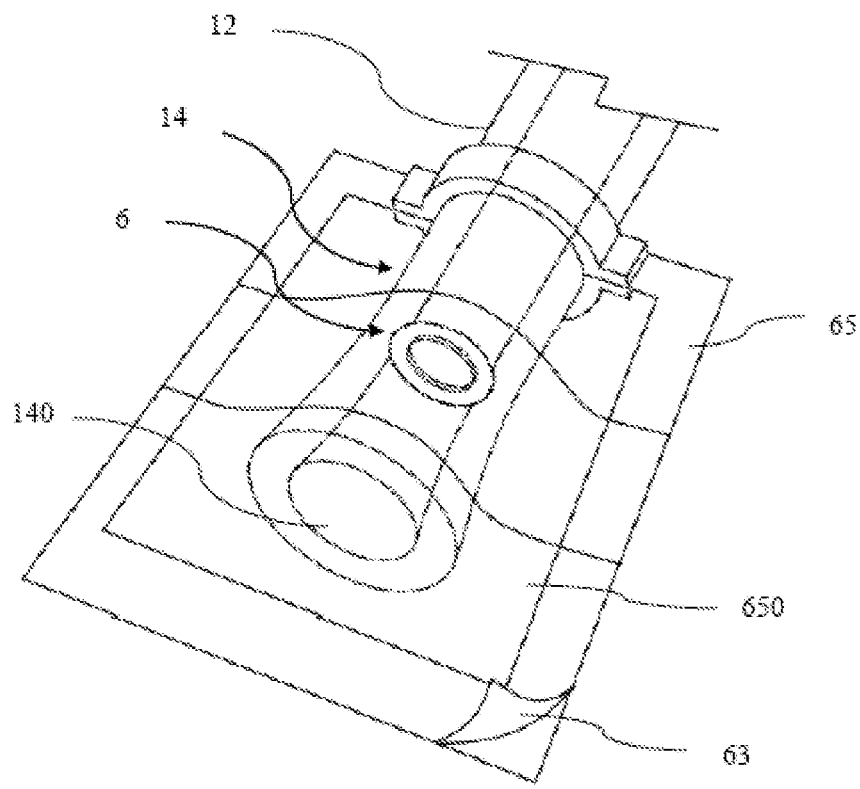
FIG. 45b is a structural schematic view of a urinary catheter tail according to Embodiment 25 of the present utility model.

Embodiment 25: as shown in FIG. 5, the traditional urethral catheterization requires urine to be drained out of the urine outlet of the urinary catheter and into containers such as the kidney basin 4 before it can be judged that the urinary catheter is placed in the bladder cavity 00. When urine 4b flows out of the urine outlet 140, it will inevitably retain and contaminate the urinary catheter tail end face 1411 at the urine outlet 140. The urine 4b retained thereon will have microorganisms entering the urine outlet proliferated, and when the drainage urine bag connector 5 is inserted, it will bring the microorganisms into the urinary catheter inner cavity 10 and cause infection by retrograde invasion into the bladder cavity 00. As shown in FIGS. 45a and 45b, in order to avoid the disadvantages of this traditional method, the urinary catheter tail 14 is provided with a hydrophobic membrane for leakage stop 62 that blocks the liquid but does not block the air from passing through the urinary catheter inner cavity 10. The outer periphery of the hydrophobic membrane for leakage stop 62 is sealably connected with an annular fixing housing 61 to form the leakage stop part 6, and the fixing housing 61 is conformally and sealably connected with the annular recess 110 of the urinary catheter inner surface 11 of the urinary catheter inner cavity 10 of the urinary catheter tail 14, partially toward the urinary catheter outer surface 12.

In order to facilitate the observation of urine 4c, at least the catheter wall in the area near the hydrophobic membrane for leakage stop 62 is transparent or partially transparent within reach of the eye.

In order to ensure that the urine outlet of the urinary catheter is not polluted for a period of time before it is butted with the drainage urine bag connector, a section of the urinary catheter tail 14 at the urine outlet 140 is closed by a sealing element 65 that is easy to open, and the urine outlet 140 is located in a protective cavity 650 sealed by the sealing element 65 that is easy to open. The easily openable sealing element 65 itself is made of a material through which air can easily pass.

The internal bladder pressure of the patient during urination is usually within 10 kPa, and a hydrophobic membrane made of PVDF, PES, PAN and other polymers having a bore diameter of 0.1-0.5 microns and a water-blocking pressure of 10-20 kPa may be used in the embodiments.

Figure 46:
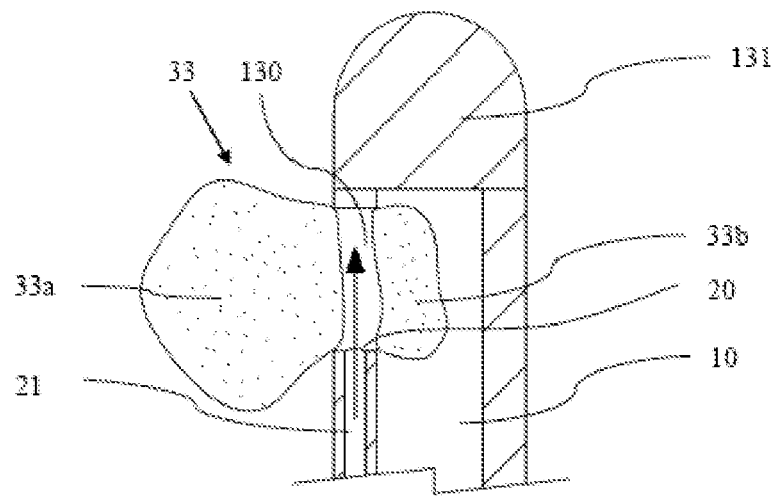
FIG. 46 is a structural schematic view of a urine inlet of a urinary catheter according to Embodiment 26 of the present utility model.
Figure 47:
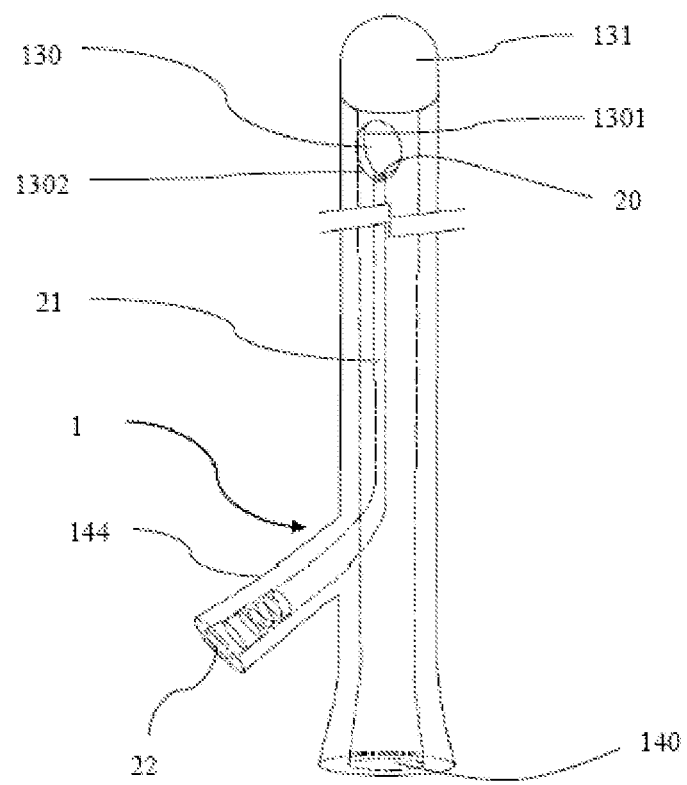
FIG. 47 is a structural schematic view of a urinary catheter according to Embodiment 26 of the present utility model.

Embodiment 26: as shown in FIGS. 46 and 47, during the indwelling of the urinary catheter, the urine inlet 130 is easily blocked by various mass substances, affecting drainage. Tests show that: Blood clots 33 can be smashed or even cut and broken by a thinner fluid jet. In this embodiment, a foreign liquid outlet 20 is provided on the tube wall 1318 between the urinary catheter inner cavity inlet 1301 and outer cavity inlet 1302; the foreign liquid outlet is connected with the foreign liquid inlet 22 of the urinary catheter tail 14 through the foreign liquid route 21 on the urinary catheter wall; the foreign liquid inlet 22 is located at the foreign liquid collateral branch 144 of the urinary catheter tail 14, which can be closed by a sealing element such as non-return valve 2.

As an alternative to this embodiment, the foreign liquid outlet 20 may also be provided in the area adjacent to and/or adjacent to the urine inlet 130, in which, the said area adjacent to the urine inlet 130 means that when the liquid is jet inside the foreign liquid outlet 20 set in such area, the liquid flow line may enter the urine inlet 130 or be tangential to the urine inlet 130.

When the urine inlet 130 is completely or partially blocked by blood clots 33, protein lumps and the like from the bladder, and urine cannot be drained or is difficult to be drained to the outside, liquid is pressurized and injected from the foreign liquid inlet 22 and ejected from the foreign liquid outlet 20, and the blockage of the urine inlet 130 is smashed, torn or deformed and displaced by a high-speed flow line to drive away from the urine inlet 130, eliminating or alleviating the blockage of the urine inlet 130, in which, the said drive away from the urine inlet 130 refers to two situations where fragments enter the urinary catheter inner cavity 10 from the urine inlet 130 or are pushed out of the urine inlet 130 back to the bladder cavity 00. FIG. 46 shows the liquid jet shown by the arrow cutting a blood clot 33 into two parts 33a, 33b, wherein the blood clot 33b enters the urinary catheter inner cavity 10 and the blood clot 33a can be pushed out of the urine inlet 130 back to the bladder cavity 00.

Figure 48:
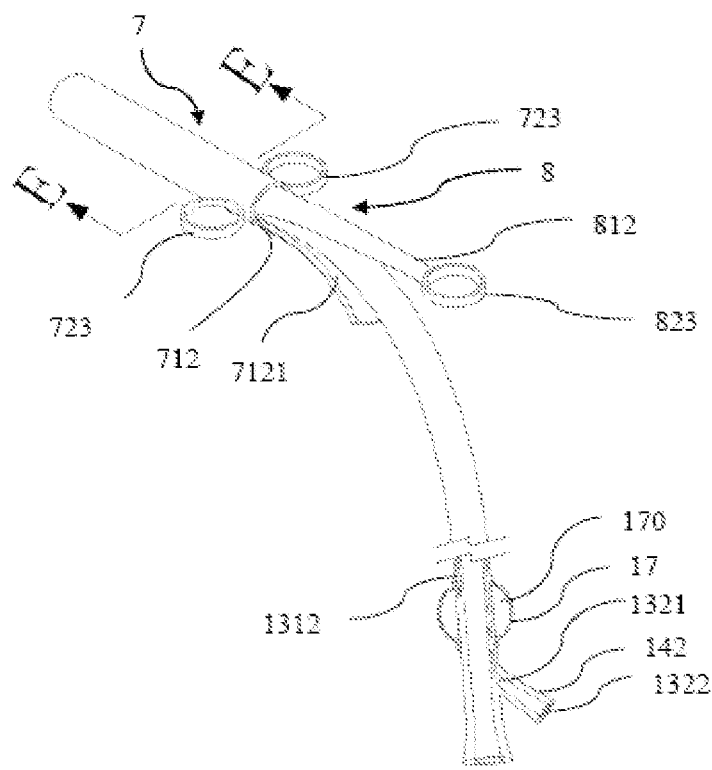
FIG. 48 is a structural schematic view of Embodiment 27 of the present utility model.
Figure 49A:
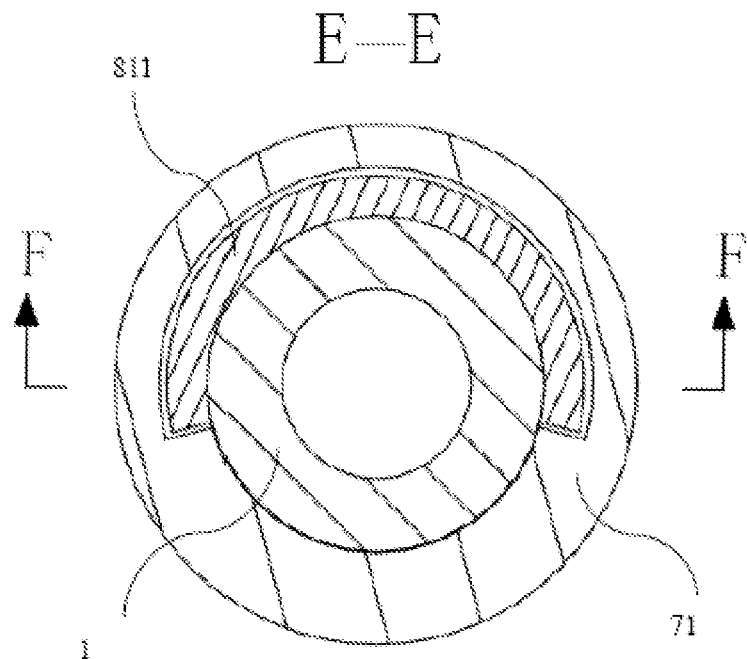
FIG. 49a is a plan view of FIG. 48 after section E-E is cut open in three dimensions according to Embodiment 27 of the present utility model.
Figure 49B:
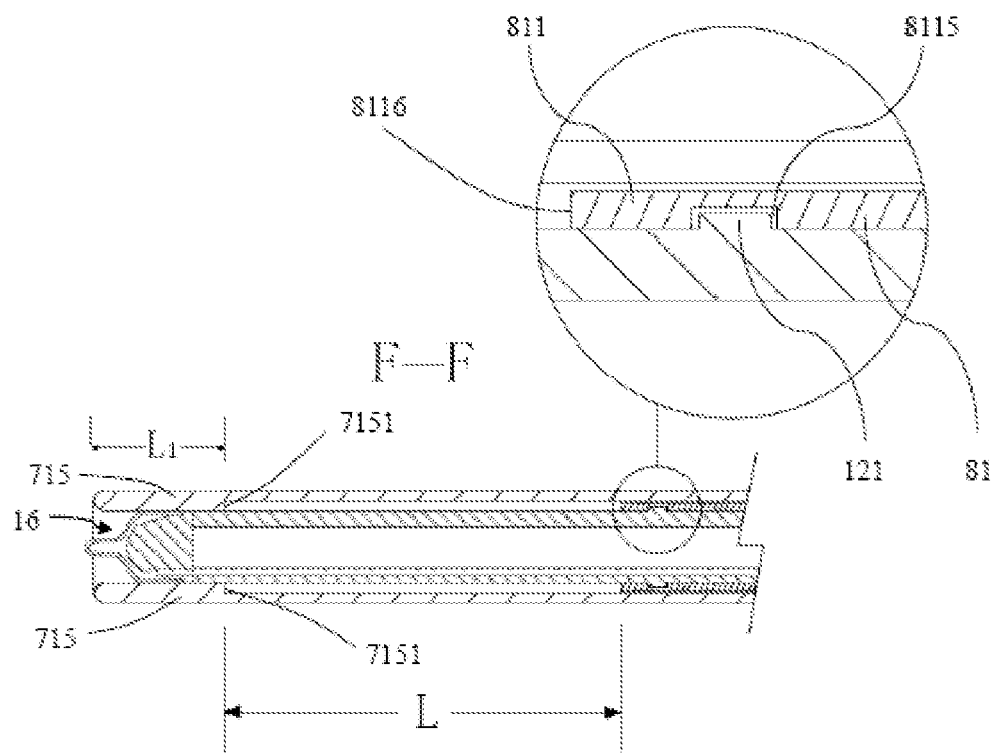
FIG. 49b is a plan view of FIG. 49a after section F-F is cut open in two dimensions according to Embodiment 27 of the present utility model.

Embodiment 27: as shown in FIGS. 48, 49a and 49b, compared with embodiments 18 and 19, it is a solution that can replace the return spring 666 and can prevent microorganisms from contaminating the urinary catheter outer surface 12 through the fixing part body through slot 714 on the fixing part body 71 of the fixing part 7. First, two fixing part finger rings 723 are provided at the fixing part body 71 of the fixing part 7 near the fixing part tail end opening 712, and one driving part tail finger ring 823 is provided at the driving member tail 812 of the driving part 8. Compared with embodiments 18 and 19, during use, when two fingers, usually index fingers and middle fingers are fit into the fixing part finger rings 723 on the fixing part 7 and the thumb of the same hand is fit into the driving part tail finger ring 823 on the tail of the driving part 8, the push-pull action can be completed with one hand, which can push the driving part 8 to move in the direction of the external urethral orifice 0100 and pull the driving part 8 to move in the opposite direction of the external urethral orifice 0100 so as to synchronously withdraw the urinary catheter from the urethra 01.

Further, the fixing part 7 is no longer provided with the fixing part body through slot 714, the driving part tip 811 of the driving part 8 is completely placed in the fixing part cylindrical hollow 70, and the arc-shaped driving part tip end face 8116 of the driving part tip 811 stops when it travels to the annular boss 7151 of the fixing part top end guide portion 715, and the distance between the two is greater than or equal to the urinary catheter length L in the bladder and urethra when the catheter is retained; further, the urinary catheter tip end 131 is provided with the thin segment 16 in the previous embodiment, and the tube wall of the urinary catheter tail 14 is sleeved with the elastic balloon 17, and the inner cavity 170 thereof is connected with the thin segment inner cavity 160 through the thin segment inner cavity route 1312; of course, the fixing part 7 can also have an openable and closable structure.

Figure 50:
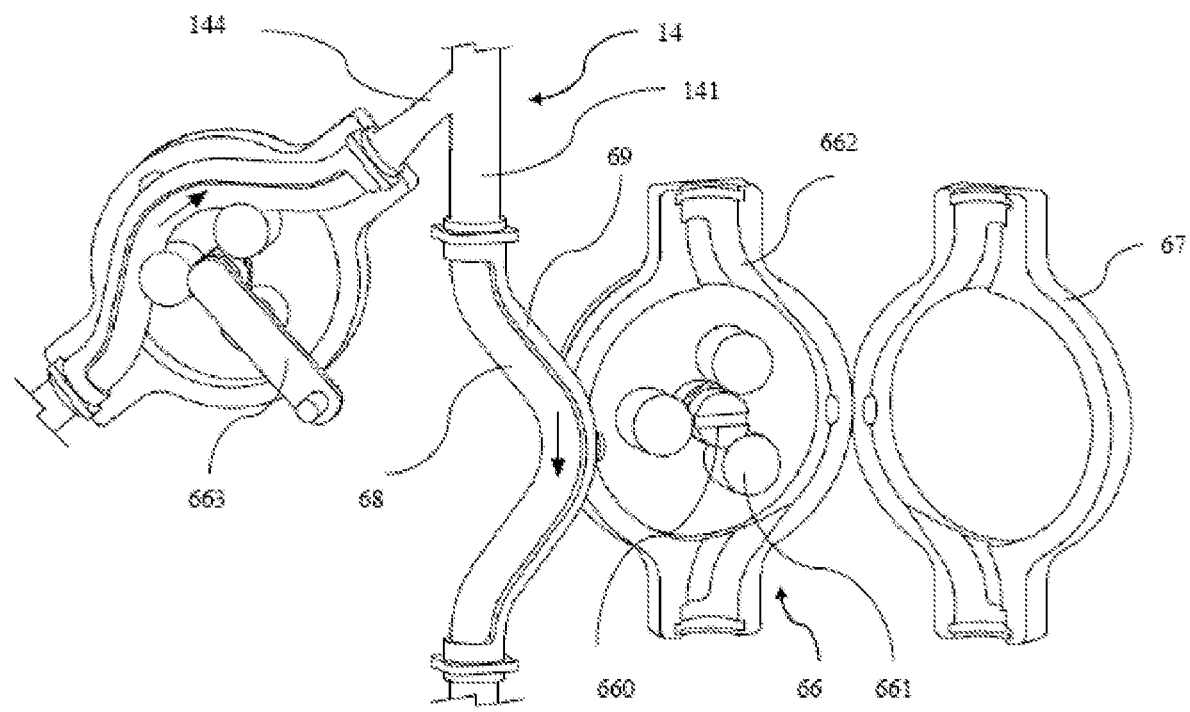
FIG. 50 is a structural schematic view of Embodiment 28 of the present utility model.

Embodiment 28: as shown in FIG. 50, in order to facilitate the active drainage of urine and the injection of foreign liquid, a part of the tube connecting the main drainage branch 141 and the foreign liquid collateral branch 144 at the urinary catheter tail is a pump tube which can be deformed and closed under local extrusion and can be restored if extrusion removed, and the said pump tube is sleeved in a curved tube bed 69 which can be directly embedded in a tube bed receiving cavity 662 on a pump body of a rotor peristaltic pump matched therewith.

The peristaltic pump matched comprises a pump body 66, a peristaltic component composed of a roller 661 and a power component composed of a rotor 660, wherein, the pump body 66 is provided with a receiving cavity 662 which can accommodate a tube bed 69 sleeved with a pump tube 68 previously described herein.

A part of the tube connecting the main drainage branch 141 corresponding to the urinary catheter inner cavity 10 at the urinary catheter tail 14 is a pump tube 68 which can be deformed and closed under local extrusion and can be restored if extrusion removed, and the said pump tube is sleeved in a curved or vertical tube bed 69 which can be directly embedded in the tube bed receiving cavity 662 on the pump body of a rotor peristaltic pump or finger peristaltic pump matched therewith, and the pump body cover 67 can be closed. The arrow on the main drainage branch 141 is the urine flow direction and the arrow on the foreign liquid collateral branch 144 is the foreign liquid flow direction.

Such method of operating urination and attracting obstruction outside the urinary catheter cavities avoids frequent opening of the connection between the urinary catheter and the drainage urine bag, which reduces the risk of retrograde infection, and the associated effect of active urination can also relieve urination weakness caused by low bladder pressure caused by various reasons to a certain extent, and can also train the bladder.

A smaller outer diameter of the urinary catheter also means a smaller inner diameter, which is usually prone to poor drainage. Although a catheter having a larger outer diameter and a larger inner diameter has a better drainage effect, the one having a larger outer diameter will bring greater urethral irritation and injury, which is a clinical dilemma. However, when a peristaltic pump outside the catheter is used to assist urination, combined with the blockage removal design described above, catheters having a smaller outer diameter can be applied to patients who need to select catheters having a larger outer diameter according to the existing experience, thus ensuring smooth drainage, eliminating blockage and removing blockage while reducing urethral irritation and injury caused by too thick catheters.

The driving force of the peristaltic pump rotor 660 can be either electric or manual, and driving the rotary handle 663 can drive the peristaltic pump to run.

The foreign liquid pump-in and urine pump-out performed at the same time significantly reduces the clinical procedures, cuts down workload of medical staff, and has a very ideal effect for catheter blockage elimination and blockage removal. In an in-vitro simulation of urinary catheter blockage in bladder, a 200 ml of the whole blood clot is placed into the artificial bladder inner cavity, and completely removed outside the urinary catheter in half an hour. Although the test used a whole blood clot far exceeding the clinical common blood clot volume, due to the attraction of the peristaltic pump, a part of the blood clot was sucked into the catheter urine inlet 130 between the inner cavity inlet 1301 and the outer cavity inlet 1302, and the impact of foreign liquid such as normal saline smashed the part of the blood clot into the catheter inner cavity 10 to be sucked away, and by repeating the procedure continuously, finally the 200 ml of the whole huge blood clot was completely removed.

What is claimed is:

1. A urinary catheter for women, comprising:
   a body tube having a urinary catheter inner surface, a urinary catheter outer surface, and a urinary catheter inner cavity inside the body tube, the body tube including:
   a urinary catheter tip including a urine inlet and configured to enter a bladder,
   a urinary catheter tail including a urine outlet and configured to be left outside the bladder when the urinary catheter is applied to the bladder,
   a urinary catheter middle section connecting the urinary catheter tip with the urinary catheter tail, wherein due to a wall thickness of the urinary catheter, the urine inlet comprises:
      an inner cavity inlet provided on the urinary catheter inner surface and being immediately adjacent to the urinary catheter inner cavity; and
      an outer cavity inlet provided on the urinary catheter outer surface, and configured to be closer than the inner cavity inlet to the bladder when the urinary catheter is applied to the bladder; and
   a fixing part configured to at least sleeve at a urinary catheter tip end of urinary catheter tip, the fixing part having independent parts, and two parts or components configured to be opened and closed, and the fixing part including:
      a fixing part body including a hollow cylinder with a fixing part top end opening and a fixing part tail end opening, the hollow cylinder being configured to allow the urinary catheter tip and at least a part of the urinary catheter middle section to pass through; and
      a protruding and integrated support leg provided on one side of the fixing part top end opening, the support leg including:
         a connecting end connecting the fixing part top end opening; and
         an oval shaped support leg free end opposite to the connecting end and distal to the fixing part top end opening, a surface of the oval shaped support leg free end being a non-planar surface concave toward the fixing part top end opening;
   wherein:
      an orthographic projection of the fixing part top end opening onto a first plane has an oval shape, the first plane being perpendicular to a central axis of the hollow cylinder, and the central axis of the hollow cylinder passing through a center of the fixing part top end opening and a center of the fixing part tail end opening; and an orthographic projection of the support leg onto a second plane includes a topmost contour line corresponding to the surface of the oval shaped support leg free end, the topmost contour line being a curved line concave away from the connecting end, and the second plane being parallel to both the central axis of the hollow cylinder and a major axis of the fixing part top end opening.

2. The urinary catheter for women according to claim 1, wherein, at least two protruding independent support legs are provided on one side of the fixing part top end opening; a support leg free end of the independent support leg is configured to be pressed against the periurethral tissue of the female external urethral orifice, so that the support legs are configured to be fixed relative a position of the external urethral orifice and allows the external urethral orifice to be enlarged.

3. The urinary catheter for women according to claim 1, wherein, the support leg is configured to be pressed against the periurethral tissue of the external urethral orifice, so that the support leg is configured to be fixed relative a position of the external urethral orifice and allows the external urethral orifice to be enlarged.

4. The urinary catheter for women according to claim 1, wherein:

a flexible urethral guide part configured to at least partially penetrate into a urethra is provided on one side of the fixing part top end opening;

the urethral guide part is a hollow body with both ends open and has a tapered shape, a guide part bottom end being configured to taper toward a guide part top end; and the guide part bottom end is sleeved outside the fixing part top end opening;

a guide part lateral surface of the urethral guide part is configured to be in contact with a urethral intima; and a guide part medial surface of the urethral guide part is configured to be in contact with the urinary catheter outer surface protruding from the fixing part top end opening.

5. The urinary catheter for women according to claim 1, further comprising:

a driving part with a rod-shaped or cylindrical body and including a driving part tip and a driving part tail, wherein, at least the driving part tip is sleeved with the fixing part body, the driving part tip and the fixing part body are in sliding fit, the driving part tail is away from the fixing part, a driving part tip inner surface of the driving part tip is provided with at least one driving part force application part, and a urinary catheter wall force bearing part is provided on a wall of the urinary catheter.

6. The urinary catheter for women according to claim 1, further comprising:

a driving part with a rod-shaped or cylindrical body and including a driving part tip and a driving part tail, wherein at least the driving part tip is sleeved with the fixing part body, the driving part tip and the fixing part body are in sliding fit, the driving part tail is away from the fixing part, a driving part tip inner surface of the driving part tip is provided with at least one driving part force application part, and a urinary catheter wall force bearing part is provided on a wall of the urinary catheter; and a return spring sleeved between the fixing part and the driving part to prevent the driving part from moving toward the fixing part top end of the fixing part.

7. The urinary catheter for women according to claim 1, further comprising:

a driving part with a rod-shaped or cylindrical body and including a driving part tip and a driving part tail, wherein:

at least the driving part tip is sleeved with the fixing part body, the driving part tip and the fixing part body are in sliding fit, the driving part tail is away from the fixing part, a driving part tip inner surface of the driving part is provided with at least one driving part force application part, and a urinary catheter wall force bearing part is provided on a wall of the urinary catheter; and the fixing part body is provided with two rings near the fixing part tail end opening, and the driving part tail is provided with at least one ring.

8. The urinary catheter for women according to claim 1, wherein, the urinary catheter tip end extends conically outward, and a urinary catheter tip end conical extension part extends from the fixing part top end opening to first penetrate into the external urethral orifice and guide the urinary catheter tip forward.

9. The urinary catheter for women according to claim 1, wherein:

an outer surface of the urinary catheter tip end is connected with a nipple-shaped flexible and hollow thin segment, the thin segment including:

a thin segment bottom connected with the urinary catheter tip end;

a thin segment top away from the urinary catheter tip end, the thin segment top being closed to outside by a blind end, and an average outer diameter between a thin segment top farthest point and a urinary catheter tip end farthest point being smaller than a maximum outer diameter of the urinary catheter tip end;

a connecting part at which the thin segment is connected with the outer surface of the urinary catheter tip end; and a thin segment dilatable part being a rest part of the thin segment other than the connecting part, wherein an inner surface of the thin segment dilatable part and a part of the urinary catheter tip end whose outer surface is covered by the thin segment dilatable part form a thin segment inner cavity; the thin segment inner cavity is connected to the outside through at least one thin segment inner cavity route the at least one thin segment inner cavity route includes at least one thin segment inner cavity route inner opening connecting with the thin segment inner cavity and at least one thin segment cavity route outer opening connecting with outside space at the urinary catheter middle section or the urinary catheter tail part, and the thin segment inner cavity route outer opening is located in an elastic balloon inner cavity of a hollow elastic balloon.

10. The urinary catheter for women according to claim 1, further comprising:

a hydrophobic membrane for leakage stop arranged at the urinary catheter tail and being configured to close the urinary catheter inner cavity to outside to prevent fluid but not air.

11. The urinary catheter for women according to claim 1, wherein:
 at least one foreign liquid outlet is provided on a tube wall of the body tube between the urinary catheter inner cavity inlet and the outer cavity inlet and/or in a region near the urine inlet; and
 the foreign liquid outlet is connected with a foreign liquid inlet on a foreign liquid collateral branch of the urinary catheter tail through a foreign liquid route on the urinary catheter wall.

12. The urinary catheter for women according to claim 1, wherein:
 a part of the body tube connecting a main drainage branch and/or a foreign liquid collateral branch at the urinary catheter tail is a pump tube, the pump tube being deformable and being configured to be closed under local extrusion and to be restored if the local extrusion removed, and the pump tube being sleeved in a curved or vertical tube bed, the tube bed being configured to be directly embedded in a tube bed receiving cavity on a pump body of a rotor peristaltic pump or a finger peristaltic pump.

13. The peristaltic pump, comprising:
 a pump body including a receiving cavity configured to accommodate a tube bed, the tube bed being configured to sleeve at the pump tube of claim 12;
 a peristaltic component; and
 a power component.

14. The urinary catheter for women according to claim 1, wherein the fixing part further includes:
 a holding portion boss extending from an outer surface of the hollow cylinder and enclosing the fixing part tail end opening, an outer diameter of the holding portion boss being larger than an outer diameter of the hollow cylinder.

\* \* \* \* \*